(12) United States Patent
Gibbs et al.

(10) Patent No.: US 12,396,804 B2
(45) Date of Patent: Aug. 26, 2025

(54) LANDMARK REGISTRATION SYSTEM FOR IMAGE-GUIDED NAVIGATION

(71) Applicant: X-Nav Technologies, LLC, Lansdale, PA (US)

(72) Inventors: Jason Gibbs, State College, PA (US); Scott A. Merritt, Green Lane, PA (US); Robert W. Emery, III, Mclean, VA (US); Pascal Kunz, Oberwil-Lieli (SE) (US); Edward J. Marandola, Gwynedd, PA (US); Christopher W. Scharff, Collegeville, PA (US)

(73) Assignee: X-Nav Technologies, LLC, Lansdale, PA (US)

( * ) Notice: Subject to any disclaimer, the term of this patent is extended or adjusted under 35 U.S.C. 154(b) by 0 days.

(21) Appl. No.: 19/027,752

(22) Filed: Jan. 17, 2025

(65) Prior Publication Data

US 2025/0228623 A1    Jul. 17, 2025

Related U.S. Application Data

(60) Provisional application No. 63/621,831, filed on Jan. 17, 2024.

(51) Int. Cl.
*G06T 7/00* (2017.01)
*A61B 34/20* (2016.01)

(52) U.S. Cl.
CPC ...... *A61B 34/20* (2016.02); *A61B 2034/2065* (2016.02)

(58) Field of Classification Search
CPC .................................................... A61B 34/20
See application file for complete search history.

(56) References Cited

U.S. PATENT DOCUMENTS 6,374,198 B1 * 4/2002 Schifa .................. G06V 30/144
                                                    703/2
7,901,348 B2 * 3/2011 Soper ............... A61B 1/000096
                                                    600/117

(Continued)

OTHER PUBLICATIONS

International Search Report and Written Opinion dated Mar. 7, 2025, 43 pages.

*Primary Examiner* — Edward Park
(74) *Attorney, Agent, or Firm* — Faegre Drinker Biddle & Reath LLP

(57) ABSTRACT

A landmark registration registers landmark points of navigation guidance information for performing a navigational guidance of a surgery procedure. The registration operation comprises a landmark point identification procedure and a landmark matching procedure. In particular, the present case is directed to automatically identifying three or more landmark points in an anatomy image by using a model according to shapes of a bone ridge depicted in the anatomy image. A graphical user interface enables interactively confirming locations of the three or more landmark points in the anatomy image. Given the identified three or more landmark points, the present case further describes interactively matching respective locations of the respective landmark points in the anatomy image with physical locations of a probe tip in anatomy according to deviation information of the probe tip. The automated identification and the interactive matching of landmark points enable generating navigational surgical guidance information with accuracy.

27 Claims, 11 Drawing Sheets

(56) References Cited

U.S. PATENT DOCUMENTS

| | | |
|---|---|---|
| 10,729,502 B1 * | 8/2020 | Wolf .............. G06Q 10/063112 |
| 2008/0013809 A1 | 1/2008 | Zhu et al. |
| 2009/0034813 A1 | 2/2009 | Dikmen et al. |
| 2012/0046536 A1 | 2/2012 | Cheung et al. |
| 2016/0331463 A1 | 11/2016 | Nötzli et al. |
| 2018/0221098 A1 | 8/2018 | Forsyth et al. |
| 2018/0252536 A1 * | 9/2018 | Dorum ............... G01C 21/3673 |
| 2022/0343504 A1 | 10/2022 | Donhowe et al. |
| 2023/0172425 A1 * | 6/2023 | Li ........................... G06T 7/00 600/109 |

* cited by examiner

LANDMARK REGISTRATION SYSTEM FOR IMAGE-GUIDED NAVIGATION

RELATED APPLICATION

The present application is related to and claims priority from U.S. Provisional Application No. 63/621,831, filed on Jan. 17, 2024, the disclosure of which is incorporated herein by reference in its entirety.

FIELD OF THE INVENTION

The present invention is directed to registering instruments, such as surgical tools, and, more specifically, a method for registering a surgical tool using a fiducial-free or limited fiducial landmark registration procedure for an image-guided navigation. The landmark registration procedure as described in the present invention represents a procedure to register one or more landmarks without use of a fiducial or using only one fiducial before performing a surgery.

BACKGROUND

Among the challenging aspects of using a surgical navigation/guidance system with accuracy is the accurate and time efficient registration of the patient's anatomy to an appropriate reference frame. The registration needs to take place at the beginning of a navigated surgical procedure. This registration process aligns the navigational equipment with respect to one or more parts of the patient's anatomy. The alignment operation is at the core of many modern surgical procedures. In examples, orthopedic robots need to learn where to make cuts and holes for knee and hip replacement, neurosurgical navigation systems need to orient the surgeon with respect to the brain anatomy or spine. In dental navigation systems and robots, there arises a need to instruct a clinician using the systems and robots where to drill into bone to insert dental implants, augment bone to allow for dental implants, or make cuts for orthognathic or prosthetic procedures after having defined the treatment through a three-dimensional plan.

There may be significant variations of the types of anatomy to be registered and forms of the technical reference frame to be registered to the anatomy. The anatomical variation comprises rigid structures and soft tissue or organs. The rigid structures further comprise bones. While bones are rigid within a bone, bones may move relative to one another, often in complex motions (e.g., the vertebrae). Soft tissue and nonrigid organs may also move and deform with surgical intervention and natural processes. In aspects, cardiac and respiratory motion causes significant local motion that hinders the registration process.

Similarly, there are many modalities of the technical reference frame to be registered according to procedures. In orthopedic knee replacement, the technical reference frame is with respect to identifiable landmarks on the knee. Often, though, the technical reference frame is a preoperative medical image in which surgical planning/treatment is performed prior to the clinical procedure. Ultrasound, MRI, PET, and CT images are examples of typical modalities in which pre-operative surgical planning is performed. In the dental procedure, some surgical treatment planning comprises pre-operative identification of an appropriate size and location for a dental implant for a failed/failing tooth.

SUMMARY

The present case generally relates to registering landmark points of navigation guidance information for performing a navigational guidance of a surgery. In particular, the present technology is directed to a pre-surgery, fiduciary-free registration procedure that comprises a landmark planning procedure and a landmark matching procedure. The landmark planning procedure either automatically and/or interactively identify one or more landmark points of at least three landmark points in an anatomic image of a patient. The landmark matching procedure comprises interactively matching respective locations in anatomy of the patient with previously identified, respective landmark points of the at least three landmark points. In particular, the landmark matching procedure comprises a clinician physically pointing to and touching a probe at respective locations to determine locations that correspond the landmark points of the patient by using a graphical user interface that tracks in real time a distance between the probe and an expected location of a landmark point. Given the matching locations of the at least three or more identified landmark points, the present case enables registering the landmark points with accuracy before a surgery.

In an embodiment, a method is disclosed for registering landmark points for image guided surgery. The method involves the steps of:
(i) identifying a location of a first landmark point of at least three landmark points in an anatomy image;
(ii) identifying, based on an anatomical feature in the anatomy image, a location of a second landmark point of the at least three landmark points in the anatomy image;
(iii) identifying, based on an anatomical feature in the anatomy image, a location of a third landmark point of the at least three landmark points in the anatomy image;
(iv) storing the identified first landmark point location, the identified second landmark point location and the identified third landmark point location;
(v) receiving probe location information corresponding to real-time locations of a probe tip on a patient's anatomy;
(vi) matching a first probe location of the probe location information with the identified first landmark point location and storing the first probe location as a first registered landmark point;
(vii) determining first deviation information based on the probe location information;
(viii) displaying the first deviation information;
(ix) matching a second probe location with the identified second landmark point location when the first deviation information is below a threshold and storing the second probe location as a second registered landmark point;
(x) determining second deviation information based on the probe location information;
(xi) displaying the second deviation information;
(xii) matching a third probe location with the identified third landmark point location when the second deviation information is below a threshold and storing the third probe location as a third registered landmark point; and
(xiii) generating, based on the first, second and third registered landmark points, navigational guidance information for performing a surgery operation on the anatomy.

The anatomy image may be a combination of intraoral scan data and computed tomography ("CT") image data.

The step of generating navigational guidance information may include the additional steps of using the first, second and third registered landmark points to correlate the positional data of a surgical tool location relative to a patient's anatomy with a CT scan of the patient's anatomy; and generating and presenting on a display during a surgical procedure a representation of a surgical tool on the CT image based on real time data received on the location of the surgical tool during a surgical operation.

The first deviation information optionally is based on at least one of (i) the first registered landmark point and (ii) the identified first landmark point location; and the identified second landmark point location.

In an embodiment the first deviation information is based on a difference between a first distance and a second distance. The first distance is the distance between the identified first landmark point location and the identified second landmark point location, and the second distance is the distance between (i) one of either the identified first landmark point location or the first registered landmark point, and (ii) the probe location information corresponding to a current location of the probe tip.

The second deviation information may be based on (a) at least one of (i) the first registered landmark point, (ii) the identified first landmark point location, (iii) the second registered landmark point, and (iv) the identified second landmark point location; and (b) the identified third landmark point location.

Optionally, the second deviation information is based on a difference between a third distance and a fourth distance, wherein the third distance is the distance between (a) one of either the identified first landmark point location or the first registered landmark point, and (b) the identified third landmark point location, and the fourth distance is the distance between (c) one of either the identified first landmark point location or the first registered landmark point, and (d) the probe location information corresponding to a current location of the probe tip.

In an embodiment, the step of receiving probe location information comprises receiving a stream of location data corresponding to the changing location of the probe tip as it moves. The first deviation information changes based on changes in the probe location information; and the second deviation information changes based on changes in the probe location information.

In one embodiment, the anatomical feature is detected by defining a mesh representation corresponding to at least a portion of a surface in the anatomy image; analyzing geometries of the mesh representation for identifying local morphological characteristics representation of anatomical features; and selecting the anatomical feature.

In an embodiment, the first location of the first landmark point corresponds to a location of a fiducial attached to the anatomy of the patient.

In an embodiment, the method involves displaying the anatomy image and interactively receiving an input in the anatomy image, the input specifying the second landmark point location of the at least three landmark points in the anatomy image.

The second location of the second landmark point may be selected to be on a crest of a bone ridge of a jawbone as determined by a trained machine learning model. The trained machine learning model predicts the crest of the bone ridge in an arch of points as along a midline of the jawbone in the anatomy image based on the anatomy image as input.

A system for registering landmark points as a pre-surgery procedure is also disclosed. The system comprises one or more processors configured to execute various operations including the following:

(i) identifying a location of a first landmark point in an anatomy image;
(ii) identifying, based on an anatomical feature detected in the anatomy image, a location of a second landmark point in the anatomy image;
(iii) identifying, based on an anatomical feature detected in the anatomy image, a location of a third landmark point in the anatomy image;
(iv) storing the identified first landmark point location, the identified second landmark point location and the identified third landmark point location;
(v) receiving probe location information corresponding to real-time locations of a probe tip on a patient's anatomy;
(vi) matching a first probe location of the probe location information with the identified first landmark point location and storing the first probe location as a first registered landmark point;
(vii) determining first deviation information based on the probe location information;
(viii) displaying the first deviation information;
(ix) matching a second probe location with the identified second landmark point location when the first deviation information is below a threshold and storing the second probe location as a second registered landmark point;
(x) determining second deviation information based on the probe location information;
(xi) displaying the second deviation information;
(xii) matching a third probe location with the identified third landmark point location when the second deviation information is below a threshold and storing the third probe location as a third registered landmark point; and
(xiii) generating, based on the first, second and third registered landmark points, navigational guidance information for performing a surgery operation on the anatomy.

The system optionally generates navigational guidance information by using the first, second and third registered landmark points to correlate the positional data of a surgical tool location relative to a patient's anatomy with a CT scan of the patient's anatomy; and generating and presenting on a display during a surgical procedure a representation of a surgical tool on the CT image based on real time data received on the location of the surgical tool during a surgical operation.

The first deviation information may be based on at least one of (i) the first registered landmark point and (ii) the identified first landmark point location; and the identified second landmark point location.

In an embodiment of the system, the first deviation information is based on a difference between a first distance and a second distance. The first distance is the distance between the identified first landmark point location and the identified second landmark point location, and the second distance is the distance between (i) one of either the identified first landmark point location or the first registered landmark point, and (ii) the probe location information corresponding to a current location of the probe tip.

The second deviation information may be based on (a) at least one of (i) the first registered landmark point, (ii) the identified first landmark point location, (iii) the second registered landmark point, and (iv) the identified second landmark point location; and (b) the identified third landmark point location.

In an embodiment, the second deviation information is based on a difference between a third distance and a fourth distance. The third distance is the distance between (a) one of either the identified first landmark point location or the first registered landmark point, and (b) the identified third landmark point location. The fourth distance is the distance between (c) one of either the identified first landmark point location or the first registered landmark point, and (d) the probe location information corresponding to a current location of the probe tip.

The receiving of the probe location information may comprise receiving a stream of location data corresponding to the changing location of the probe tip as it moves. The first deviation information changes based on changes in the probe location information. The second deviation information also changes based on changes in the probe location information.

In the system, the anatomical feature is preferably detected by defining a mesh representation corresponding to at least a portion of a surface in the anatomy image; analyzing geometries of the mesh representation for identifying local morphological characteristics representation of anatomical features; and selecting the anatomical feature.

The identified first landmark point location in an embodiment may correspond to a location of a fiducial attached to the anatomy of the patient.

In an embodiment of the system, the processor may be further configured to execute operations comprising displaying the anatomy image; and interactively receiving an input in the anatomy image, the input specifying the second landmark point location in the anatomy image.

In an embodiment, the second landmark point location is selected to be on a crest of a bone ridge of a jawbone as determined by a trained machine learning model. The trained machine learning model predicts the crest of the bone ridge in an arch of points as along a midline of the jawbone in the anatomy image based on the anatomy image as input.

A non-transitory computer-readable recording medium having stored computer-executable program instructions is disclosed which, when executed by at least one processor, cause a computer system to execute operations comprising:
 (i) identifying a location of a first landmark point in an anatomy image;
 (ii) identifying, based on an anatomical feature detected in the anatomy image, a location of a second landmark point in the anatomy image;
 (iii) identifying, based on an anatomical feature detected in the anatomy image, a location of a third landmark point in the anatomy image;
 (iv) storing the identified first landmark point location, the identified second landmark point location and the identified third landmark point location;
 (v) receiving probe location information corresponding to real-time locations of a probe tip on a patient's anatomy;
 (vi) assigning a first probe location of the probe location information to the identified first landmark point location and storing the first probe location as a first registered landmark point;
 (vii) determining first deviation information based on the probe location information;
 (viii) displaying the first deviation information;
 (ix) matching a second probe location with the identified second landmark point location when the first deviation information is below a threshold and storing the second probe location as a second registered landmark point;
 (x) determining second deviation information based on the probe location information;
 (xi) displaying the second deviation information;
 (xii) matching a third probe location with the identified third landmark point location when the second deviation information is below a threshold and storing the third probe location as a third registered landmark point; and
 (xiii) generating, based on the first, second and third registered landmark points, navigational guidance information for performing a surgery operation on the anatomy.

The computer-readable recording medium may be programmed to provide the operational step of generating navigational guidance information including using the first, second and third registered landmark points to correlate the positional data of a surgical tool location relative to a patient's anatomy with a CT scan of the patient's anatomy; and generating and presenting on a display during a surgical procedure a representation of a surgical tool on the CT image based on real time data received on the location of the surgical tool during a surgical operation.

In an embodiment, the computer-readable recording medium may be programmed to determine the first deviation information based on a difference between a first distance and a second distance. The first distance is the distance between the identified first landmark point location and the identified second landmark point location, and the second distance is the distance between (i) one of either the identified first landmark point location or the first registered landmark point, and (ii) the probe location information corresponding to a current location of the probe tip.

In an embodiment, the computer-readable recording medium may be programmed to determine the second deviation information based on a difference between a third distance and a fourth distance. The third distance is the distance between (a) one of either the identified first landmark point location or the first registered landmark point, and (b) the identified third landmark point location. The fourth distance is the distance between (c) one of either the identified first landmark point location or the first registered landmark point, and (d) the probe location information corresponding to a current location of the probe tip.

This Summary introduces a selection of concepts in a simplified form, which is further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the following description and, in part, will be apparent from the description, or may be learned by practice of the disclosure.

BRIEF DESCRIPTION OF THE DRAWINGS

For the purpose of illustrating the invention, the drawings show a form of the invention that is presently preferred. However, it should be understood that the invention is not limited to the precise arrangement and instrumentalities shown in the drawings.

DETAILED DESCRIPTION

Figure 1:
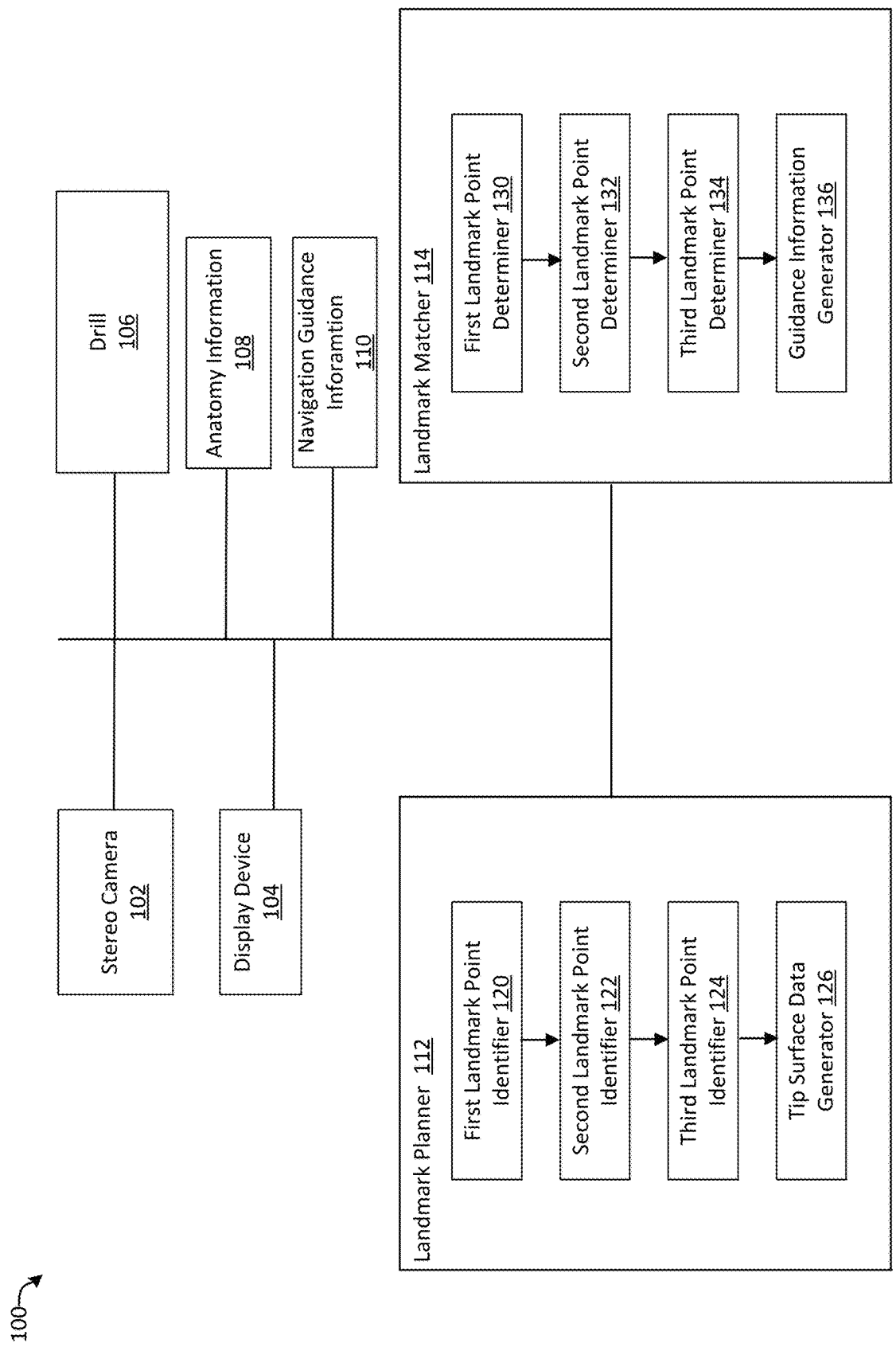
FIG. 1 illustrates an overview of an embodiment of a registration system for planning and determining landmark points according to the present invention.

In the following detailed description, references are made to the accompanying drawings that form a part hereof, and in which are shown by way of illustrations specific embodiments or examples. These aspects may be combined, other aspects may be utilized, and structural changes may be made without departing from the present disclosure. Embodiments may be practiced as methods, systems or devices. Accordingly, embodiments may take the form of a hardware implementation, an entirely software implementation, or an implementation combining software and hardware aspects. The following detailed description is therefore not to be taken in a limiting sense, and the scope of the present disclosure is defined by the appended claims and their equivalents.

Recent advances made in technologies for registering the patient's anatomy have enabled performing computer-navigated procedures with improved accuracy and efficiency. In aspects, there are two distinct methods for providing dental registration: a registration procedure using a fiducial and a registration procedure without using a fiducial. Both types of registration operations respectively include 1) a landmark planning procedure, followed by 2) a landmark matching procedure.

One conventional dental registration procedure with a fiducial uses a clip with embedded fiducials that is attached to the patient's teeth. In aspects, the clip has an optical patterned tracker (e.g., a patient tracker) mounted to it. An exemplary embodiment of a clip is disclosed in U.S. Pat. No. 9,844,324, which is incorporated herein by reference in its entirety.

A conventional planning procedure using a clip requires that the patient has stable teeth to mount the clip on the patient's teeth. Patients for a dentist/oral surgeon in the dental implantology domain are commonly those that have issues with stability of a tooth. In many cases, the patients are those with missing teeth or might need a complete reconstruction of a jaw (i.e., "a full arch case"). The planning procedure requires placing the clip inside the patient's mouth during the acquisition of the diagnostic cone beam computed tomography ("CBCT") scan. When a patient has already been imaged without the clip installed, the planning procedure necessitates another scan of CBCT, which would result in the patient receiving an extra radiation dose.

In some cases, the computed tomography ("CT") imaging is performed separately from the clinician. Accordingly, coordination of the CBCT with the placement of the needed clip can be burdensome in operation.

The clip includes three metal spheres that are placed at exact known distances from one another. The conventional system identifies these spheres in the CBCT image to identify the important locations in the CBCT reference frame.

During a surgery, the clinician places the clip back into the same position it was in during the CBCT image. Accordingly, the three metal spheres in the clip are rigidly affixed to the patient's anatomy in the same position they were in the CT image. The surgery tracking system detects a patient tracker, which is attached to the clip and determines the position of the three metal spheres. As such, the surgery tracking system associates the observed patient tracker to the metal spheres inside the mouth of the patient. The surgical planning is associated with the three spheres in the CT image, thereby correlating the live patient's anatomy to the preoperative plan through a chain of rigid body transformations.

In some aspects, a registration process may be performed without using metal fiducial spheres attached to the patient's anatomy. The registration process involves identifying at least three points in the CBCT scan and also the corresponding locations of the at least three points in the patient's anatomy to enable both the pre-operative planning and the matching procedure for a live surgery with accuracy.

The user, during the planning procedure, identifies landmark points in the CBCT scan. The user subsequently matches the landmark points with respective locations in the anatomy. In aspects, the landmark planning is performed preoperatively by clicking on points in the three-dimensional or two-dimensional slices in the CBCT scan. For a dentate patient, the clinician may identify sharp cusps of teeth as a landmark for planning during the registration. These sharp cusps may be identified directly in the CBCT image, or in other modalities that have been aligned to the CBCT image, namely an intraoral scan mesh. Intraoral scans, unlike CT, provide very high-resolution representations of the surfaces of teeth and are not prone to scatter effects that result from metal objects in the CT field of view. Intraoral scans, however, do not provide any information about the bone or tooth condition or anatomical features beneath the skin. Accordingly, other examples include a combination of the intraoral scans and CT, providing a more complete digital representation of the patient's anatomy. The intraoral scan depicts the visible teeth surfaces, while the CT scan provides the hidden anatomy below the gumline and tooth enamel.

During surgery, the planned landmarks on the patient need to be matched in the patient's anatomy for registration in the surgical navigation system. The matching procedure is accomplished by physically touching the corresponding points of landmarks on the patient's anatomy with a specially tracked probe, a tip of a drill, and the like. By touching the corresponding points, the surgical navigation system establishes association between the location of the tip of the probe (e.g., a drill tip) with the patient tracker that is rigidly attached to the patient. Once at least three of these points are identified for matching, a stable registration is defined between the landmark points preoperatively identified in the CBCT and the same "real" points on patient's anatomy as observed by the surgical navigation system. Additional points beyond three are not necessary but can be used as "checks" or additional estimates to provide the matching with more accuracy.

As should be appreciated, the conventional landmark registration procedure comprises additional steps as compared to the conventional registration procedure that uses a clip. In the operations without the clip, the efficacy (accuracy) of the registration is dictated by the users' ability to precisely identify landmarks both in CT and on the patient.

The benefit of the procedure without use of the clip for dental surgical navigation becomes apparent in cases where patients are completely lacking teeth. Without teeth, there is no suitable place to rigidly affix the clip during CT acquisition.

The convention landmark registration process that does not use a clip may also pose challenges to the user with respect to identifying landmark locations with accuracy because of the reasons as described as followings.

First, rigid landmarks may be located on the bone below the gumline, requiring the detachment of the gums from the bone to access the bone. Minimizing the amount of detachment required is desirable from a minimally invasive surgical perspective.

Second, patients who have been without teeth for a period of time exhibit loss of bone, resulting in an increasingly smooth, homogenous bone surface. When looking at such bone (e.g., edentulous jaws), it is difficult for the clinician to locate discernable landmarks. This is a problem for a method which is predicated on finding such landmarks.

Accordingly, accuracy of landmark point registration becomes reduced when the user cannot accurately identify a point in CT and locate that corresponding location with a probe tip on the patient's anatomy. Because of the challenges posed by edentulous jaws, the current landmark registration methodology used in surgical navigation registration becomes challenging to attain planning and matching landmarks with accuracy.

In general, correctness of a landmark-based registration is not easily evaluated until the completion of the registering of at least three landmark points. Once a full registration has completed, a probe can be manipulated along the anatomy, which is visually represented in the navigation system. If the anatomy that is depicted in the surgical navigation unit during this "System Check" correlates to the position of the probe on the anatomy, when assessed at various locations and orientations, the accuracy of the registration can be assured. Unfortunately, in most cases this assessment cannot happen until all three points have been registered. And, if the registration is not accurate, it can be difficult to assess which point(s) may have been registered in error. This uncertainty may result in longer registration times in feature-devoid anatomical cases such as edentulous patients.

The underlying challenge in conventional landmark registration (i.e., a combination of the landmark planning and the landmark matching) includes the need for the clinician to identify points on the anatomy based on their knowledge, without imposing constraints using the CT image and on the patient. The challenge particularly surfaces in edentulous cases but may also be present in dentate cases. Conventional surgical navigation systems may require use of landmark points that are on the surface of an identified anatomical component. Accordingly, when the bone is segmented in the CT image, the clinician may need to identify some point that is on the surface of the bone. During surgery, unless the clinician drills or cuts into the bone/teeth the probe would also need to define points on the surface of the bone/teeth. Such a constraint on the landmark points being on surface leaves many degrees of freedom for the clinician to manually perform the landmark registration with accuracy.

As discussed in more detail below, the present disclosure relates to registering landmark points for surgical operation upon a patient use a navigational surgery guidance system. In particular, the present technology is directed to performing a task of registering landmark points according to two subtasks before a navigated surgery takes place: a landmark planning procedure followed by a landmark matching procedure. During a landmark planning procedure, the system automatically identifies three landmark points based on a given CBCT scan data and/or CT scan data. Additionally, or alternatively, a clinician interactively selects three or more landmark points in scan image data of a patient during the landmark point planning procedure without using a clip or a fiduciary.

During the landmark matching procedure (i.e., the registration procedure), a clinician selects the three or more landmark points by pointing a probe (e.g., a tip of a drill) at actual places of anatomy of the patient. During the landmark matching procedure for a dental surgery, the clinician uses a drill tip with a sensor to point to respective landmark points that have been specified during the landmark planning procedure. Given the sequence of operations of the landmark planning and the landmark matching procedures, the present technology enables registration of data for providing a navigational surgery with accuracy.

The present technology provides interactive operations that enables the clinician to improve understanding about exact locations of the respective landmark points in the patent's anatomy prior to completion of registering the three landmark points. The improved understanding of the exact locations by the clinician enables the clinician to operate the drill with accuracy during the surgery procedure.

In aspects, the registration process according to the present technology comprises the following steps of landmark planning: identify a single landmark that can be reliably found on the patient in the patient's CT (point Number 1) and at least two other points in the patient in CT (points Number 2 and Number 3, etc.). The registration process further comprises the following steps of landmark matching: determining first landmark point on patient (point Number 1) by matching the first identified landmark point during the landmark planning to a physical location in the patient's anatomy, identify second landmark point (point Number 2) with pre-identification feedback pointing the drill 106 at a location in the anatomy of the patient, and identify third (and optionally more) landmark(s) (point Number 3, etc.).

In aspects, the landmark registration process according to the present technology is applicable for registering landmark points on many different bone or rigid structures, such as a leg bone, with accuracy for a surgery operation. While the following discussion primarily refs to features related to a patient's mouth for an oral surgical procedure, those skilled in the art would appreciate its applicability to other anatomical structures of a patient.

FIG. 1 illustrates an overview of an embodiment for planning and matching landmark points according to the present invention. In aspects, an embodiment of a navigational surgery guidance system 100 comprises stereo camera 102, display 104, drill 106, anatomy information 108, navigation guidance information 110, landmark planner 112, and landmark matcher 114. The stereo camera 102 captures frames of image data, as video data, of the drill 106 as a clinician (e.g., a user) operates the drill 106 on a patient during or prior to a dental surgery procedure. In aspects, the stereo camera 102 captures the video data of the operational scenes in stereo to enable generating three-dimensional locations of the drill 106 with accuracy based on a differential in stereo viewing angles used by the stereo camera 102. The display 104 includes a graphical user interface to interactively calibrate the drill 106.

The drill 106 comprises a drill tool that the clinician uses to perform a dental surgery procedure on the patient. In aspects, a navigational surgery guidance system performs calibration of identifying a location of the drill 106 with accuracy by enabling a clinician to point and touch the drill 106 at a location of a landmark point during landmark registration.

The anatomy information 108 indicates anatomy of the patient. In aspects, the anatomy information comprises dental cone beam computed tomography ("CBCT") scan data in at least one of two-dimensional and three-dimensional slice forms and computed tomography ("CT") scan data.

The landmark planner 112 interactively receives landmark point data that specify points in the anatomy information 108 (i.e., the anatomy) of the patient and generates tip surface data as planning of landmark points. In aspects, the landmark planner 112 comprises a series of interactive operations to perform a series of operations to perform planning of landmark points (i.e., locating desired landmark points in the CT scan for use in the registration process). In aspects, the landmark planner 112 comprises first landmark point identifier 120, second landmark point identifier 122, third landmark point identifier 124, and tip surface data generator 126.

In aspects, the clinician identifies sharp cusps of teeth on which to register as a landmark for planning. These may be identified directly in the CBCT image, or in other modalities that have been aligned to the CBCT image, namely an intraoral scan mesh.

Figure 2:
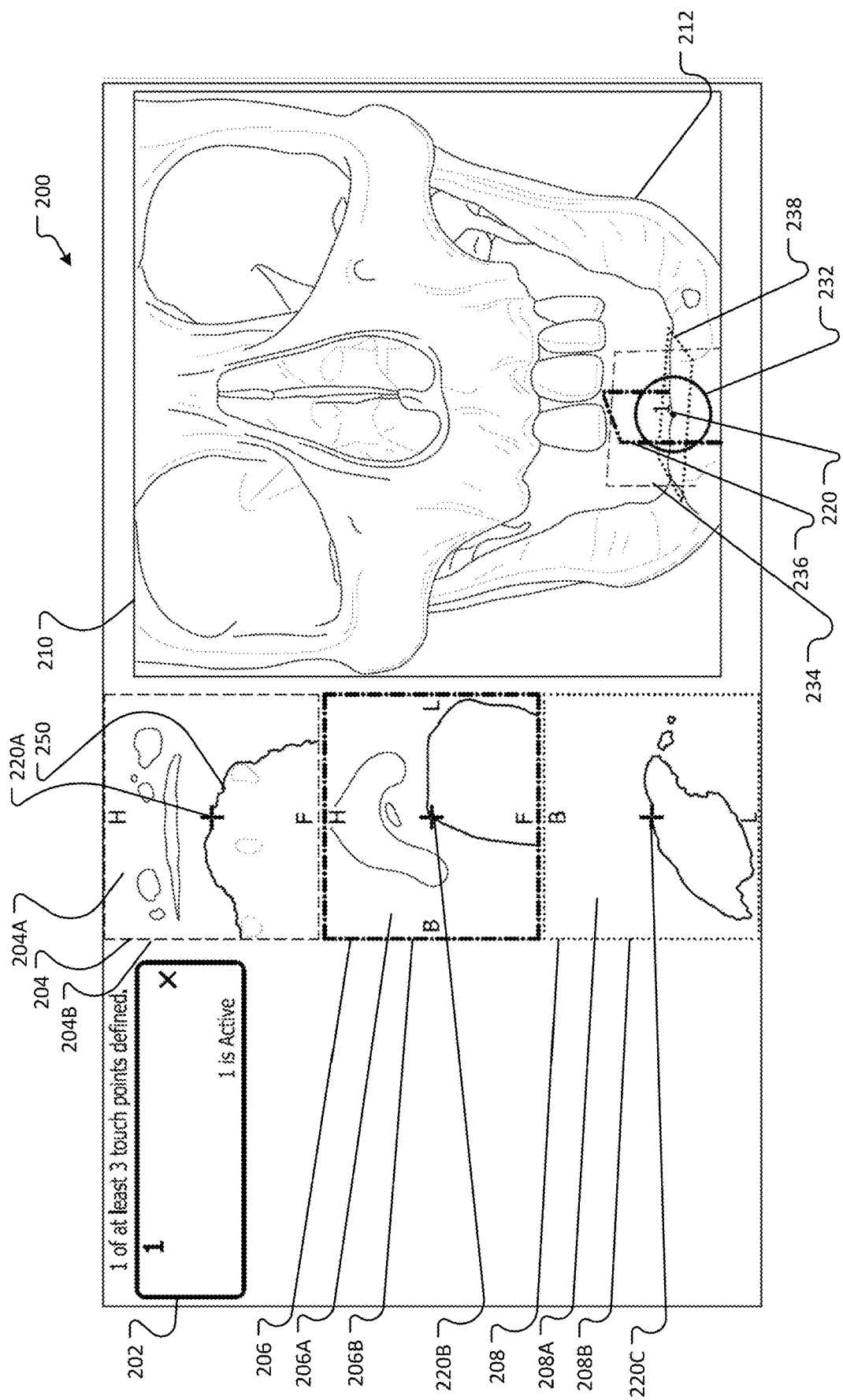
FIG. 2 illustrates graphical user interface showing a graphical image of the system while locating a first landmark point in a CBCT image during a planning procedure according to an embodiment of the invention.

The first landmark point identifier 120 interactively identifies a first landmark point in the anatomy information 108 of the patient (see, the graphical user interface as shown in FIG. 2). In examples, in edentulous patients, the crest of the bone ridge on the midline, is a reference point that can be identified using other anatomical landmarks (the lips, nose, chin, etc.). Dentists/oral surgeons are trained to identify the "midline" of the patient. The midline on the bone would result in an "arch" of points along the bone. If the user is restricted to the "crest" of the bone ridge, then the two-dimensional search along an arch becomes a single point.

In aspects, this crest on the bone ridge may be automatically identified by using a trained machine learning model to predict and propose this point along the midline (e.g., such as adding a highlighted point in the CT scan where the system determines the midline is on the crest). The model identifies local morphological characteristics based on creating a mesh representation of the tooth or bone structure and then analyzing the mesh geometries for local morphological characteristics. Vertices (or points) in the mesh would show up as an isolated extreme value (e.g., a mountain peak as compared to a ridge line). In one embodiment, the system analyzes the vertices in a mesh and determines which of those are critical points. When a critical point is found, the system then examines the Hessian matrix to determine if the critical point is a peak rather than on a ridge. A Hessian matrix is known to those skilled in the art, see for example, https://en.wikipedia.org/wiki/Hessian_matrix, which is incorporated herein by reference in its entirety. In some other aspects, the user may also manually identify it in the manner currently done—without any constraint or may identify a midline and therefore manually identify that point on the arch via a "slider" or other user interface (UI) element that selects such a point along the arch or given either automatic or user input of the midline, such a point can be automatically identified.

At least two additional landmark points may be automatically identified by a machine learning model or a set of rules for identifying the second and third landmark points in an anatomy image. Additionally, or alternatively, the two other landmark points may be interactively identified by a user (e.g., the clinician). In one embodiment, the landmark points are automatically identified at a fixed distance from first "single" landmark point but are constrained to be at the crest of the bone ridge. Because CT coordinate systems have defined orientations of patient anatomy (left/right, inferior/superior, anterior/posterior) the most inferior/anterior location can be identified on triangles in a segmentation of an anatomical regions (e.g., bone mesh, or teeth meshes). In this way, points that are along a "ridge" (a degree of freedom) and at a given three-dimensional distance from the first landmark point can be automatically identified. (The center of a crest might also strongly correlate with the center of the panoramic curve along the dental arch with the intersection of the segmented bone).

It is contemplated that a combination of the above may be beneficial, i.e., the system determines and depicts on a graphical display a proposed landmark based on the above procedure and the user is then given the ability to adjust the position based on the user's desire, such as to account for the actual anatomical conditions that are present that the proposed landmark might interfere with during subsequent registration.

Figure 3:
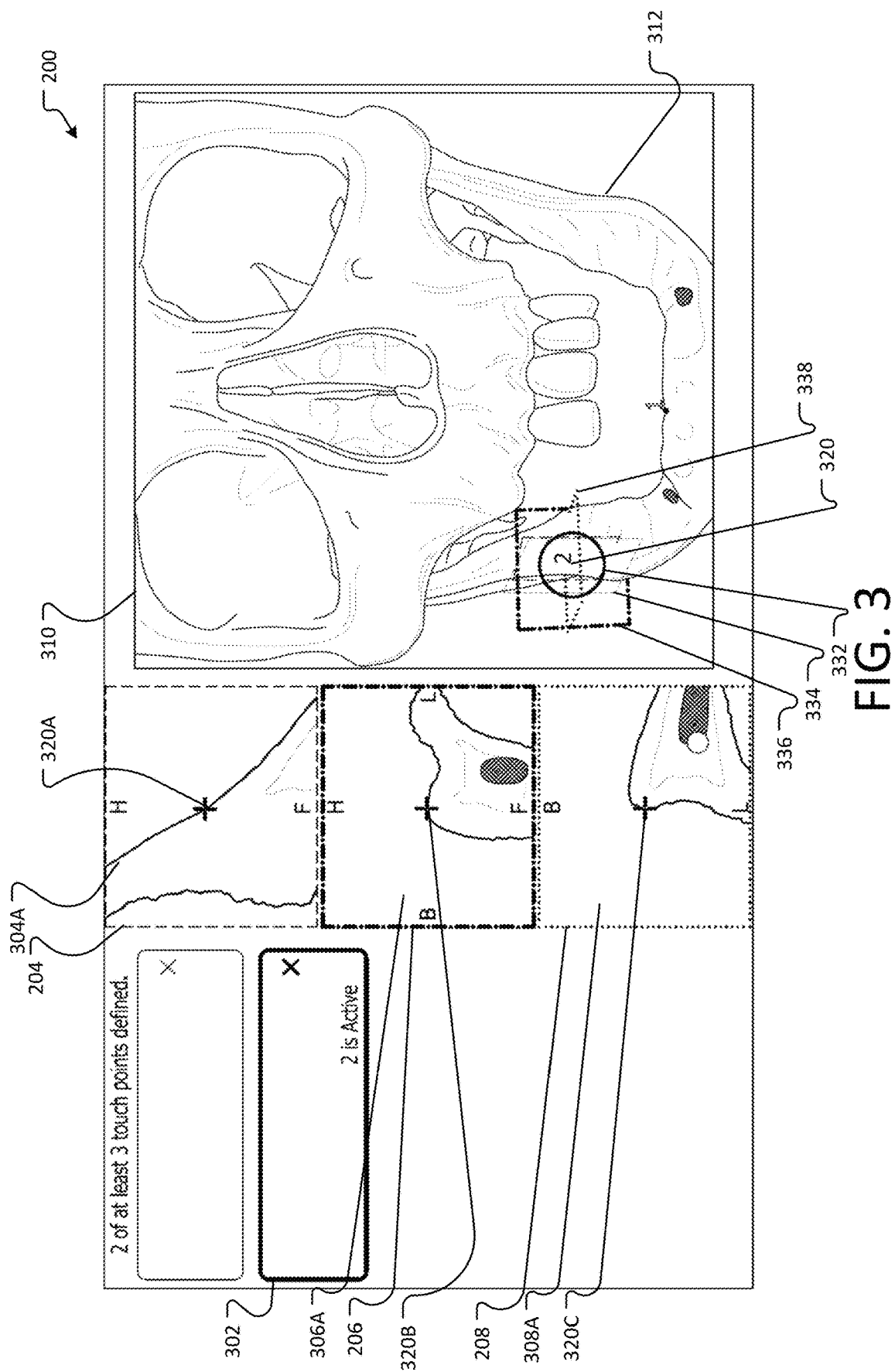
FIG. 3 illustrates the graphical user interface of FIG. 2 depicting an example graphical image of the system while locating a second landmark point during the planning procedure according to an embodiment of the invention.

The second landmark point identifier 122 interactively identifies a second landmark point in the anatomy information 108 of the patient (see the graphical user interface as shown in FIG. 3).

Figure 4:
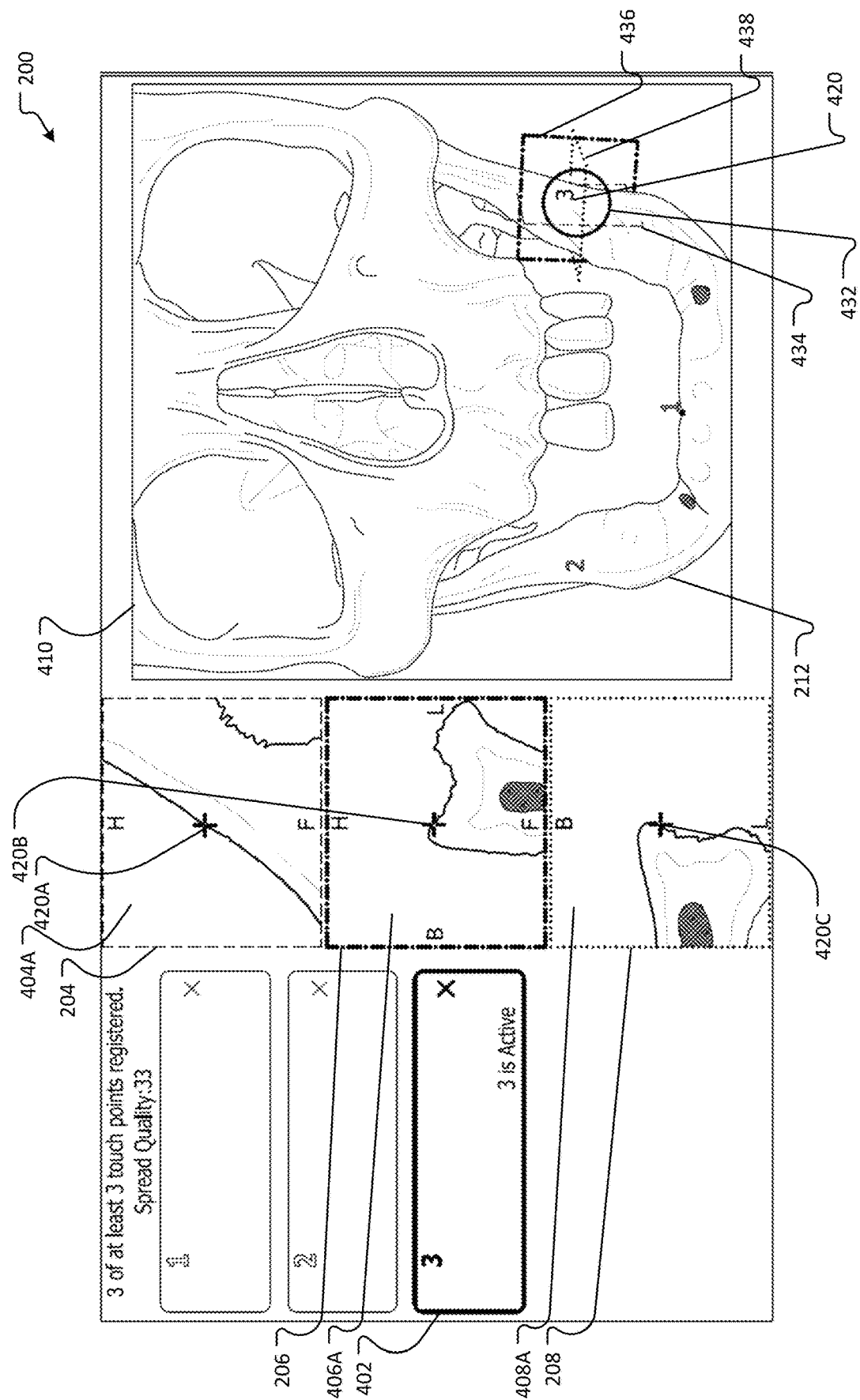
FIG. 4 illustrates the graphical user interface of FIG. 2 depicting an example graphical image of the system while locating a third landmark point during the planning procedure according to an embodiment of the invention.

The third landmark point identifier 124 interactively identifies a third landmark point in the anatomy information 108 (See the graphical user interface as shown in FIG. 4). The tip surface data generator 126 generates tip surface data comprising the first, second, and third landmark points.

The landmark matcher 114 interactively matches landmark point data with respective physical locations in the patient's anatomy and generates guidance information for use in navigating surgery operations. In aspects, the landmark matcher 114 comprises a first landmark point determiner 130, a second landmark point determiner 132, a third landmark point determiner 134, and a guidance information generator 136.

Figure 5:
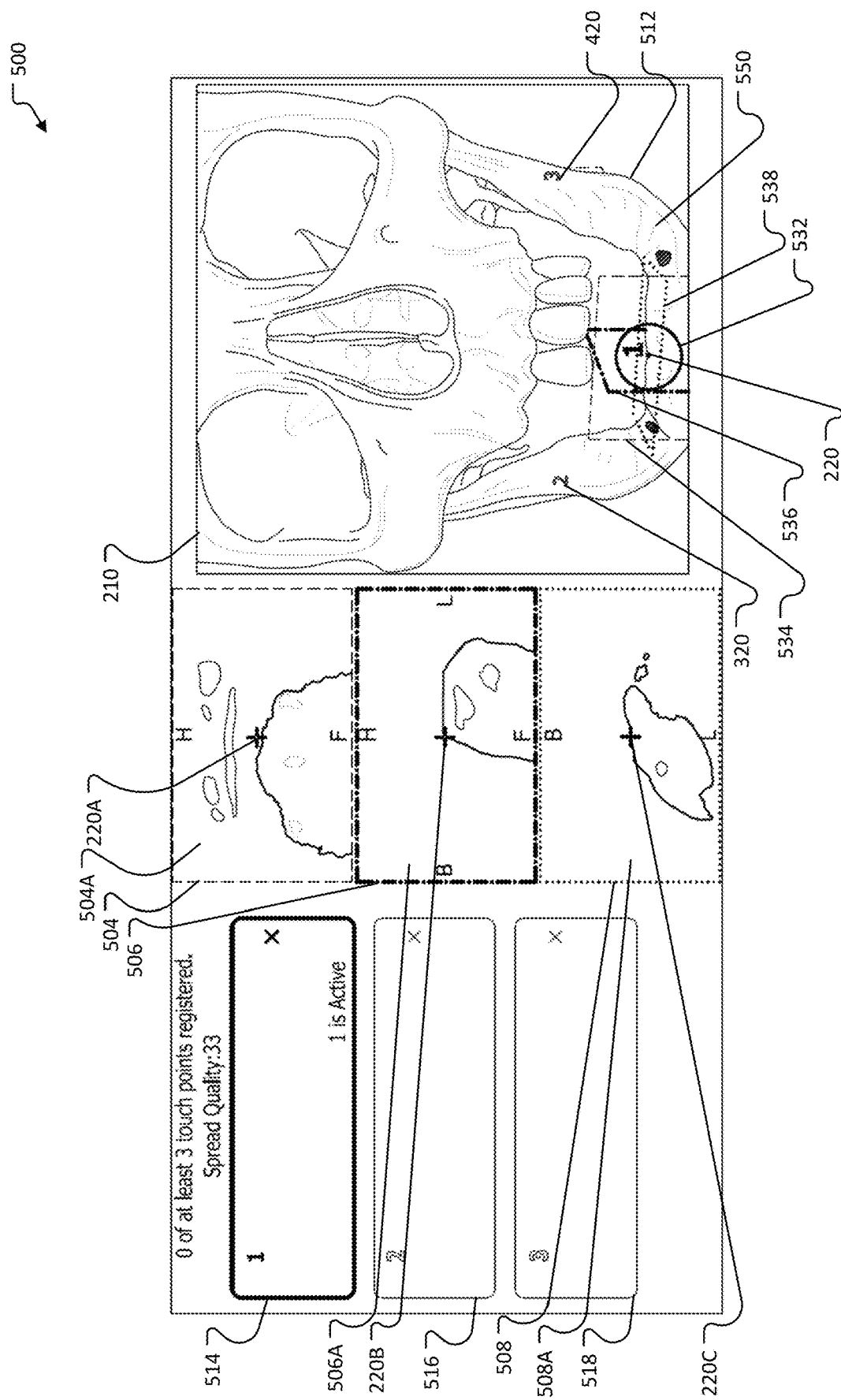
FIG. 5 illustrates the graphical user interface of FIG. 2 depicting an example graphical image of the system while registering a first landmark point on a CBCT image of a patient during a matching procedure according to an embodiment of the invention.

The first landmark point determiner 130 interactively determines a first landmark point according to a location in the anatomy of the patient where the user is physically pointing to and touching a drill tip of a drill. (See the graphical user interface 500 as shown in FIG. 5).

In aspects, during a surgery, the system identifies the first landmark point on the patient. The first landmark point may be directly identified by the clinician marking the first landmark point using a probe or drill tip. It may also be automatically identified if such a point has some greater curvature or "pointiness" than surrounding anatomy through sensors such as a depth sensor or stereo cameras to assess the anatomical structure. In aspects, the midline point is on a distinctively identifiable anatomical "point." The midline point may be automatically highlighted, identified, or provide guidance in the surgical navigation system through onscreen cues or audible feedback. As discussed above, it is contemplated that the user may adjust the position that the system automatically selects.

Figure 6:
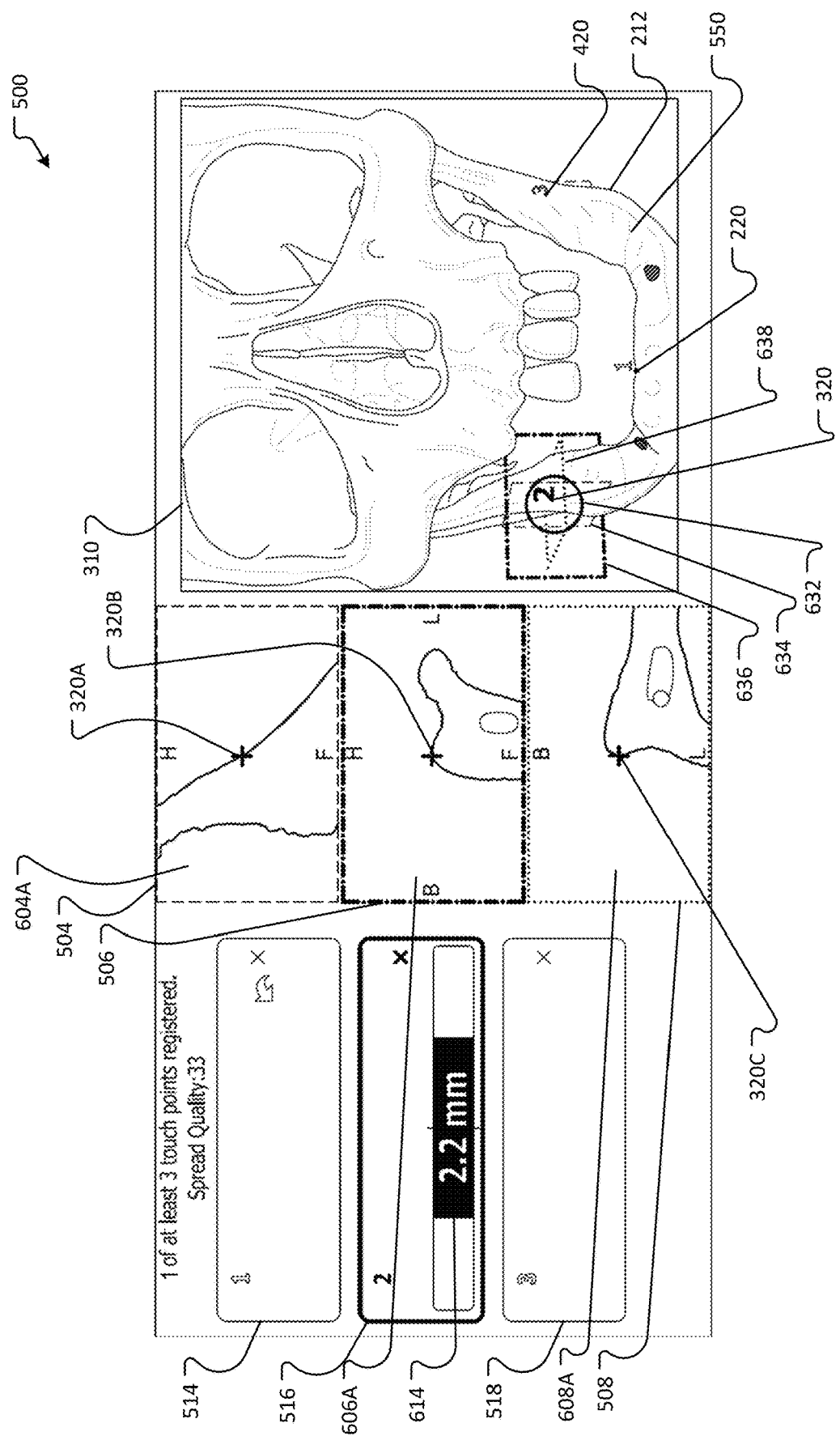
FIG. 6 illustrates the graphical user interface of FIG. 2 depicting an example graphical image of the system while registering a second landmark point during the matching procedure according to an embodiment of the invention.
Figure 7:
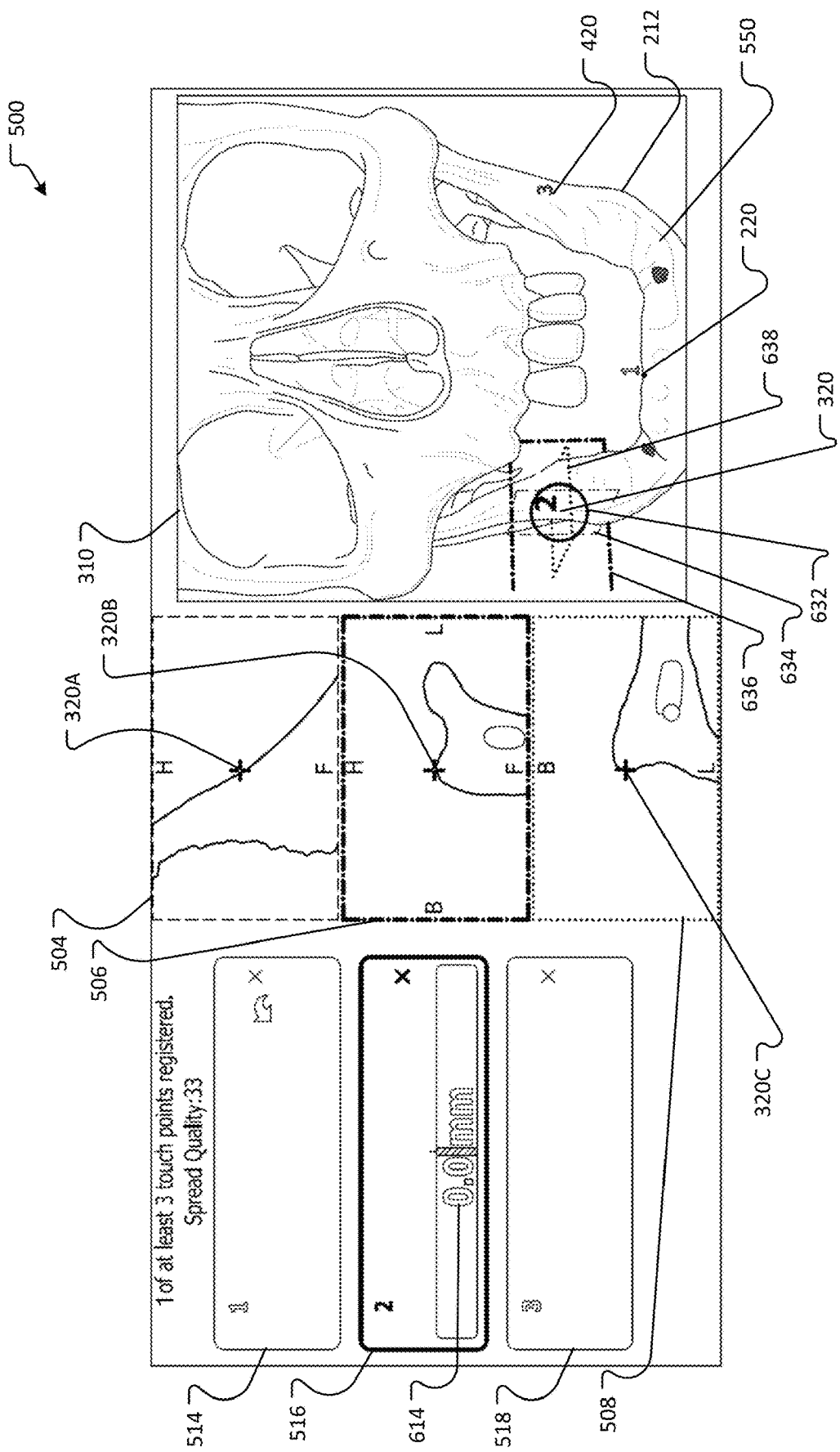
FIG. 7 illustrates the graphical user interface of FIG. 2 depicting an example graphical image of the system while registering a second landmark point during the matching procedure according to an embodiment of the invention.

The second landmark point determiner 132 interactively determines a second landmark point according to a drill tip that is physically pointing to and touching a location in the anatomy of the patient according to guidance given on a screen by a graphical user interface (e.g., the graphical user interface 500 as shown in FIG. 6 and FIG. 7).

Figure 8:
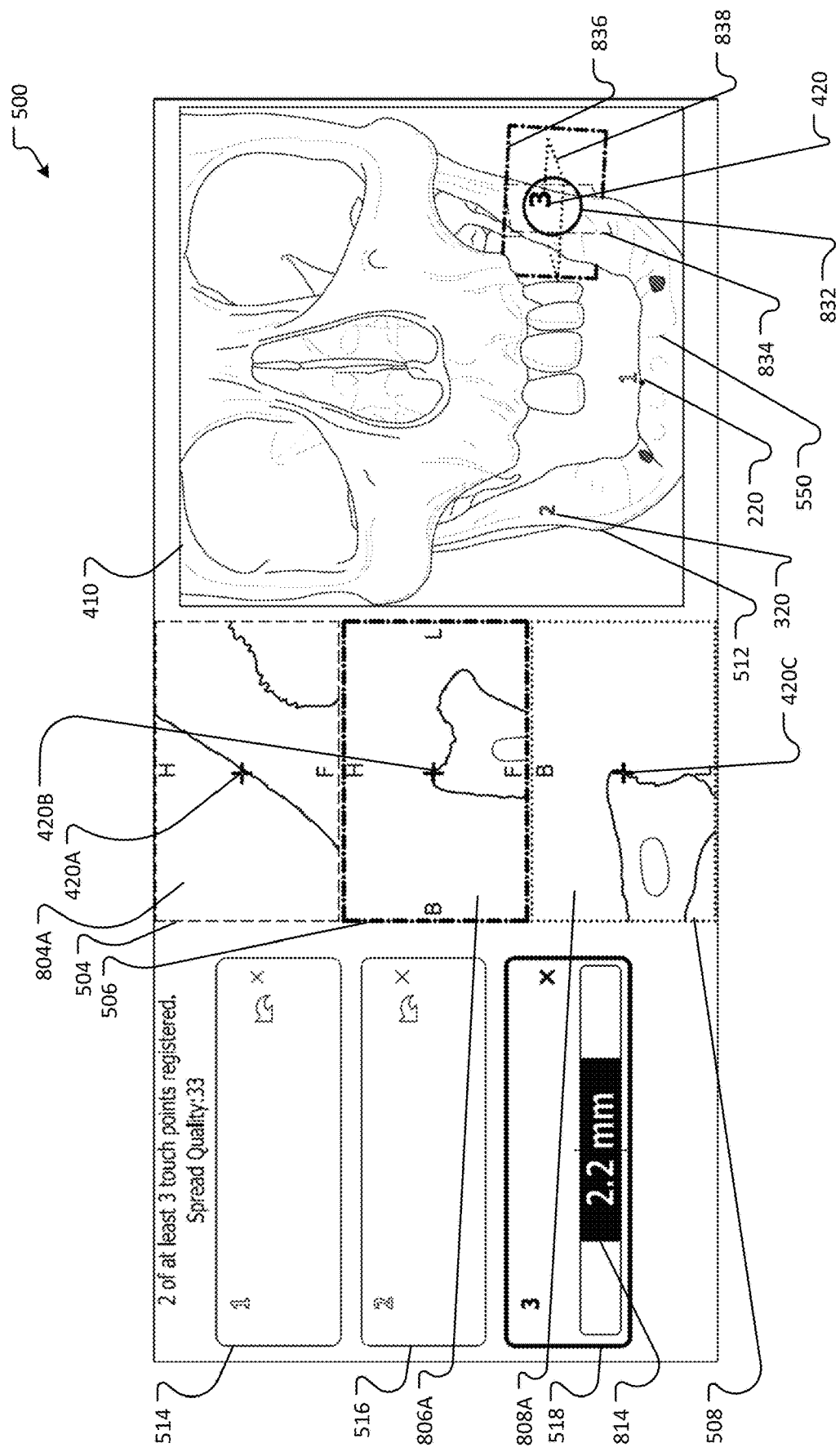
FIG. 8 illustrates the graphical user interface of FIG. 2 depicting an example graphical image of the system while registering a third landmark point during the matching procedure according to an embodiment of the invention.
Figure 9:
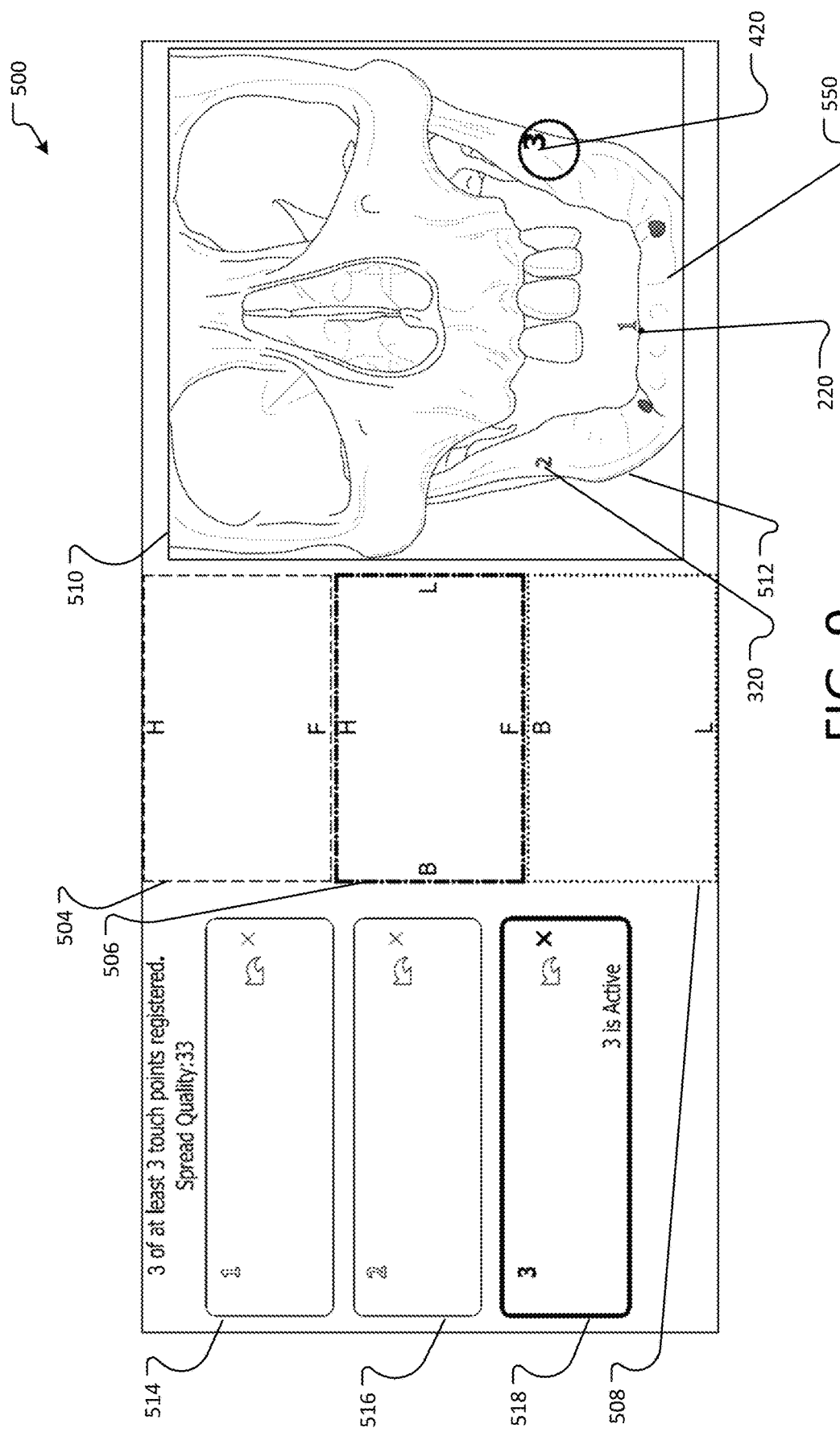
FIG. 9 illustrates the graphical user interface of FIG. 2 depicting an example graphical image of the system at the completion of the registering of the third landmark point during the matching procedure according to an embodiment of the invention.

The third landmark point determiner 134 interactively determines a third landmark point according to a drill tip that is physically pointing to and touching a location in the anatomy of the patient (e.g., the graphical user interface 500 as shown in FIG. 8 and FIG. 9).

Conventional surgical navigation systems provide feedback only after the registration of the landmark points are completed. In contrast, in the present system as discussed in more detail below, in order to assist the clinician in locating in real-time the landmark points for matching, the system relays or imposes constraints on the location of landmark points based on the previously identified landmark points from the identification steps (planning procedure). For example, once a first landmark point is located and matched by the clinician, the present system identifies the two or more remaining landmark points on a virtual patient anatomy based on the first landmark point. The clinician may provide their own mental constraints, e.g., "I identified this point on the ridge of the bone" or "I identified this point on a tooth cusp." The constraints may also be guided by the mathematical constraints of selections of landmark points in the CT scan data. Examples of the mathematical constraint in the CT include the first point and second point being separated by a predetermined three-dimensional (Euclidean) distance. Use of the mathematical constraint reduces the scope of searching for a landmark point from anywhere on the bone to anywhere on the ridge (by choosing a point on the crest of the ridge). In particular, use of the mathematical constraint helps identifying a specific point on the ridge in that region of the jaw that is a fixed distance from the first landmark point.

The present surgical navigation system may provide the measurement of the distance from the fixed landmark point without using an external measuring tool. Once the first landmark point is registered (i.e., it is located by the system in 3D space), the system may compute, in real time, a distance between a probe tip and the location of the first landmark point. Since the respective locations of the second and third landmark points have already been identified using CT scans during the planning procedure, the system can determine the distance between the probe location and the second (third, etc.) landmark points that were located during the planning procedure. The system supplies this information to the clinician to help the user attempt to identify the intended respective locations of the second (and third) landmark point by moving the probe tip inside the patient's month while monitoring the computed distance between the probe tip and the previously identified second landmark point from the planning stage. That is, the system also knows where the second, third, etc. landmarks are supposed to be from the first landmark based on the prior planned CT scan locations. By reducing the degrees of freedom of where the landmark point is supposed to be located, this greatly assists the clinician in locating that landmark point. For example, using a distance indicator that provides real-time onscreen feedback (e.g., the distance indicator 814 as shown in FIG. 8), the user can more readily move the probe tip to the anticipated location The system enables the user to more quickly and accurately locate the second and third landmark points.

In aspects, the determination of the first landmark point may generate a sphere in space where the second landmark point could be located mathematically according to the computed distance of the second landmark point (identified in the planning procedure) from the first landmark point. The system may impose a constraint on the sphere that the identified second landmark point is on a tooth (or bone) surface. Thus the anticipated location of the second landmark point may be constrained to a location on or feature of the anatomy (e.g., the tooth). Without the constraints of the distance and the surface, the user would have to ensure that the landmark points are on an exact cusp on a tooth identified as the second landmark point. The constraints as available. enable the user to narrow potential locations of the second landmark point.

The process for the third (and further) landmarks is similar to the second landmark, except that with each additional landmark to be registered, there are more constraints placed upon the location of the new landmark (i.e., the calculated distance from registered first and second landmarks). The largest deviation (in absolute value) of the probe tip's distance from the anticipated location of the third landmark is what is most driving the correctness of the probe's current point, so this is what is reported in the gauge (e.g., the distance indicator 814 as shown in FIG. 8 indicates, as an error distance as a difference of (i) a distance between the registered first landmark point and the previously identified third landmark point 420 and (ii) a distance between the registered first landmark point and the actual location of the probe tip as the user moves the probe tip inside the patient's mouth. The difference becomes zero when locations of the previously identified third landmark point 420 and the probe tip coincide). In this way, the clinician is given the distance as a single value to minimize, indicating the appropriateness of the potential landmark point for registration. As the clinician moves the drill in space the point which drives this error distance may change. They may minimize the error to landmark '1' but increase it to landmark '2', in which case the error distance to landmark would drive the distance reported in the gauge. In this way the clinician as an operator of the system has instant feedback on the appropriateness of the landmarks in the observable metric of "distance from registered points vs planned distance between points" prior to registering each landmark point 2-N (where N is the total number of landmarks to be registered) and well before registering all points.

Once the registration is complete for at least three points, the present system may subsequently retrieve and use the navigation guidance information 110 to generate and present navigational guidance during a surgery. In particular, the navigational guidance may generate and present, in real time, a difference between a location of a probe (e.g., a drill) and an expected location for performing the surgery with accuracy. The presentation of the navigational guidance may include but is not limited to displaying, speaking, and/or providing vibration to alert a state to the clinician who performs the surgery.

As will be appreciated, the various methods, devices, applications, features, etc., described with respect to FIG. 1 are not intended to limit the system 100 to being performed by the particular applications and features described. Accordingly, additional controller configurations may be used to practice the methods and systems herein and/or features and applications described may be excluded without departing from the methods and systems disclosed herein.

Additionally, or alternatively, the present system enables a user to identify a first landmark point of at least three landmark points by using a fiducial (e.g., a screw or similar locatable device placed on the patient) or by interactively identifying the midline or an existing single tooth as the first landmark point. In aspects, the at least three landmark points are not aligned in a line. Given the identified first landmark point, the system may automatically identify locations of the other landmark points through computation. In some other aspects, a graphical user interface of the present system enables the user to interactively select (e.g., by clicking locations in the CBCT image using a mouse) at least the first landmark point. When the user points the probe tip to a location of the identified first landmark point before the surgery for registration, the present system may automatically or at least guide the user to locate other landmark points of the at least three landmark points for registration.

FIG. 2 illustrates an exemplary graphical user interface that is useful in the present invention. The graphical user interface includes a series of windows that depict various images of a pertinent part of a patient that will be involved in a subsequent surgical operation. The interface facilitates identifying locations of landmark points in the CBCT image during a planning procedure according to an embodiment of the invention. The landmark points will be subsequently registered to locations in a "live" CT image of the patent during a subsequent matching procedure just prior to surgery.

In an embodiment, the graphical user interface 200 preferably includes a first landmark indicator 202, a first window 204 depicting a front-facing enlarged CBCT image 204A generated along a first reference plane 234, a second window 206 depicting a side-facing enlarged CBCT image 206A generated along a second reference plane 236 that is orthogonal to the first reference plane 234, a third window 208 depicting a downward-facing enlarged CBCT image 208A generated along a third reference plane 238 that is orthogonal to the first and second reference planes 234, 236, and a front-view CBCT image 210 (although this view can be oriented different ways depending on the user's desired perspective).

The first landmark indicator 202 represents an interactive indicator for locating a first landmark point 220 using a probe (e.g., a drill tip) during a planning procedure in order to identify the first landmark location in the CBCT image of the patient. In aspects, the first landmark indicator 202 when highlighted (or otherwise identified as "active") during the planning procedure indicates that the first landmark point 220 is active for identification on the front-view CBCT image 210. The first landmark indicator 202 may be activated either by the user selecting it (for example, such as by clicking a graphical "button" or clicking a check box) or may automatically be activated as part of the procedure (i.e., it is automatically selected when it is time for that step to become active).

The front-facing enlarged CBCT image 204A includes a cross marker 220A that corresponds to the first landmark point 220 in the front-view CBCT image 210 of the patient's anatomy 250. A border around the first window 204 of front-facing enlarged CBCT image 204A preferably corresponds to a front-facing (first) reference plane 234 as shown in the front-view CBCT image 210. The border may be colored or include other identifying indicia that correspond to the first reference plane 234. For example, the border 204B of the front-facing enlarged CBCT image 204A might be green in the display and the first reference plane 234 might be shaded green or include a green border. This assists the user in identifying which images correspond to which reference planes. For ease of reference in the figures, the border is shown as dashed lines which correspond with the dashed lines depicting the first reference plane 234. In aspects, the CT image of patient's anatomy 250 may also include locations of bone, nerves, blood vessels, and other features of the anatomy in various colors or shades.

In aspects, the respective CBCT images in the first window 204, the second window 206, and the third window 208 represent interactive images that enable the clinician (user) for specifying a seed or planned point of a landmark point by providing additional contextual image information of the seed point. That is, the images show the location as a cross marker or other suitable indicator where the user has located the mouse cursor (or other graphical user interface point device) is located on the CBCT image of the patient's anatomy in the three orthogonal planes. The interactive display allows the user to hover over a location with the a cursor while the system continuously updates the display with contextual information depicting the location of the cursor in the three image planes until the user selects the location by a double-click, for example.

When the user subsequently moves the cursor over the image after a seed point is selected, the cross markers (i.e., parts 220A, 220B, and 220C) show the seed point as it was previously selected, again to provide context information to help assist the clinician in properly defining suitable landmark points.

The side-facing enlarged CBCT image 206A includes a cross marker 220B that corresponds to the first landmark point 220 in the front-view CBCT image 210. As with the first window 204, the border 206B of the second window 206 for the side-facing enlarged CBCT image 206A preferably has indicia to depict a correspondence with the second reference plane 236 in the front-view CBCT image 210. For simplicity a dash-dot line pattern for the border around the second window 206 is used to indicate correspondence with the side-facing (second) reference plane 236 shown in the front-view CBCT image 210.

The downward-facing enlarged CBCT image 208A includes a cross marker 220C that corresponds to the first landmark point 220 in the front-view CBCT image 210. Again, indicia are used to depict correspondence of the third window 208 with the third reference plane 238 in front-view CBCT image 210. For simplicity a dotted line pattern is used as the border 208C around the third window 208 to correspond to the downward-facing (third) reference plane 238 shown in the front-view CBCT image 210.

The front-view CBCT image 210 illustrates a front view of the patient's anatomy as created from a CT scan of the patient, preferably obtained prior to surgery. The front-view CBCT image 210 also illustrates an image of the patient's jawbone 212, the first landmark point 220 (e.g., at a point marked as '1' in FIG. 2), the circular indicator 232, the front-facing reference plane 234, the side-facing reference plane 236 and the downward-facing reference plane 238.

The jawbone 212 illustrates an image of the jawbone of the patient. In aspects, the first landmark point 220 is interactively selected on the jawbone 212 in the front-view CBCT image 210 during the landmark planning procedure as discussed previously. The first landmark point 220 represents a first landmark point of the three or more landmark points in the landmark planning procedure. A circular indicator 232 may provided to represent a highlight marker in which a center of the circle corresponds to the first landmark point 220. The circulator indicator 232 identifies the landmark point that is currently active for identification during the landmark planning procedure.

FIG. 3 illustrates the graphical user interface 200 with an example graphical image of the system during the planning procedure for locating a second landmark point according to an embodiment of the invention. In aspects, the graphical user interface 200 comprises a second landmark indicator 302, a front-facing CBCT image 304A in the first window 204, a side-facing CBCT image 306A in the second window 206, a downward-facing CBCT image 308A in the third window 208, and a front-view CBCT image 310.

The second landmark indicator 302 represents an interactive indicator for selecting a second landmark point 320 (identified in the front-view CBCT image 210 by the number "2") for planning, the first landmark point 220 having already been identified. In aspects, similar to the first landmark indicator, the second landmark indicator 302 is highlighted in a manner that indicates that the second landmark point selection process is active for identification of the second landmark point on the front-view CBCT image 210. The second landmark indicator 302 may be activated either by the user selecting it or automatically as part of the procedure. Since the first landmark indicator 202 is no longer active, it is indicated on the display as inactive (such as not highlighted or marked with indicia indicating it is completed (e.g., a check mark).)

The front-facing CBCT image 304A includes a cross marker 320A that corresponds to the second landmark point 320 in the front-view CBCT image 210. As discussed above with respect to FIG. 2, each of the borders around the first window 204, second window 206 and third window 208 includes indicia that corresponds the images in the applicable window with a corresponding one of a front-facing reference plane 334, side-facing reference plane 336 (orthogonal to the first reference plane), and a down-facing reference plane 338 (orthogonal to the first and second reference planes) shown in the front-view CBCT image 210. As discussed above, for ease or reference, the borders for the different windows use different dashes and dots to show a correlation.

The side-facing CBCT image 306A includes cross marker 320B that corresponds to the second landmark point 320 in the front-view CBCT image 210.

The downward-facing CBCT image 308A includes cross marker 320C that corresponds to the second landmark point 320 in the front-view CBCT image 210.

As discussed above with respect to FIG. 2, the front-view CBCT image 210 illustrates the patient's anatomy with the second landmark point 320 (e.g., at a point marked as '2' in FIG. 3), the circular indicator 332, the front-facing reference plane 334 at the second landmark point, the side-facing reference plane 336 at the second landmark point and the downward-facing reference plane 338 at the second landmark point. In aspects, the circular indicator 332 represents a highlight marker in which a center of the circle corresponds to the second landmark point 320.

The second landmark point 320 is interactively selected on the jawbone 212 (or other location) in the front-view CBCT image 210 during the landmark planning procedure. The second landmark point 320 represents the second landmark point of the three or more landmark points in the landmark planning procedure.

FIG. 4 illustrates the graphical user interface 200 with an example graphical image of the system during the of planning procedure for locating a third landmark point according to an embodiment of the invention. In aspects, the graphical user interface 200 comprises a third landmark indicator 402, a front-facing CBCT image 404A in the first window 204, a side-facing CBCT image 406A in the second window 206, a downward-facing CBCT image 408A in the third window 208, and a front-view CBCT image 410.

The third landmark indicator 402 represents an interactive indicator for selecting a third landmark point 420 (identified in the front-view CBCT image 210 by the number "3") for planning, the first and second landmark points 220, 320 having already been identified. In aspects, the third landmark indicator 402 is highlighted in a manner as described above such that it indicates that the third landmark point selection process is active for identification of the third landmark point on the front-view CBCT image 410. Since the first and second landmark indicators 202, 302 are no longer active, they are indicated on the graphical user interface 200 as inactive (such as not highlighted or marked with a check mark).

The front-facing CBCT image 404A includes a cross marker 420A that corresponds to the third landmark point 420 in the front-view CBCT image 210. As discussed above with respect to FIG. 2, the borders around the first, second and third windows include indicia to correlate each window with a corresponding one of a front-facing first reference plane 434, side-facing second reference plane 436 (orthogonal to the first reference plane), and a down-facing third reference plane 438 (orthogonal to the first and second reference planes) shown in the front-view CBCT image 210.

The side-facing CBCT image 406A includes a cross marker 420B that corresponds to the third landmark point 420 in the front-view CBCT image 210.

The downward-facing CBCT image 408A includes a cross marker 420C that corresponds to the third landmark point 420 in the front-view CBCT image 210.

The front-view CBCT image 210 includes the third landmark point 420 (e.g., at a point marked as '3' in FIG. 4), the circular indicator 432, and the first, second and third reference planes 434, 436, 438. In aspects, the circular indicator 432 represents a highlight marker in which a center of the circle corresponds to the third landmark point 420.

The third landmark point 420 is interactively selected on the jawbone 212 (or other location) in the front-view CBCT image 410 during the landmark planning procedure. The third landmark point 420 represents the third landmark point of the three or more landmark points in the landmark planning procedure.

As mentioned above, the system, preferably, automatically identifies one or more landmark points of the first, second and third landmark points. In examples, the system identifies the second and third landmark points along a ridge of the jawbone at a predetermined distance from a primary midline point. The primary midline point corresponds to the first landmark point selected for planning. Additionally, or alternatively, the system provides an interactive user interface for the clinician to interactive select one or more landmark points of the first, second, and third landmark points as identification for the landmark planning.

Additionally, or alternatively, the system identifies a location of the first landmark point (e.g., the first landmark point 220 as indicated in FIG. 2) based on a location of a fiducial placed in the patient's mouth. Given the identified location of the first landmark point, the system automatically identifies respective locations of the second landmark point 320 and the third landmark point 420 in the front-view CBCT image 210. The respective locations may be constrained by the system to be located on the patient's anatomy, such as a surface of a tooth or a bone structure, at a predetermined distance from the location of the first landmark point. For example as discussed above the anatomy can be analyzed by the system (such as analyzing the segmentation of the teeth) to locate potential points usable at landmarks further constrained that all three potential points do not lie along a linear line.

Turning now to the next stage of the registration procedure, when the patient is ready for surgery, the clinician needs to tie or register the planning CT model that includes the previously identified landmarks during the landmark planning procedure to the live CT images of the patient. Referring to FIG. 5, a graphical user interface 500 is shown on a display (monitor). The interface 500 is preferably the same or similar to the graphical user interface 200 used in during the planning procedure, although it could be different. During the matching procedure, a CBCT scan of the patient is again shown on the display as the front-view CBCT image (illustrated in FIG. 5 on the righthand side window). Similar to the planning procedure, the display in the matching procedure includes enlarged images (shown in the center of the GUI in FIG. 5) taken along three orthogonal planes that will depict the CBCT image at the "active" locations where the user is attempting to locate and register the first, second and third landmarks. The left side of the interface 500, preferably, includes the indicators which correlate to particular landmarks that are being located.

More specifically, in one embodiment, the graphical user interface 500 comprises a first landmark indicator 514, second landmark indicator 516 and a third landmark indicator 518, a first window 504 depicting a front-facing enlarged CBCT image 504A generated along a first reference plane 534, second window 506 depicting a side-facing enlarged CBCT image 506A generated along a second reference plane 536 that is orthogonal to the first reference plane 534, a third window 508 depicting a downward-facing enlarged CBCT image 508A generated along a third reference plane 538 that is orthogonal to the first and second reference planes 534, 536, and a front-view CBCT image 210 (although this view can be oriented different ways depending on the user's desired perspective). As discussed with respect to the graphical user interface 200, the graphical user interface 500 includes indicia, such as coloring of shading of the border of the first, second and third windows 504, 506, 508 to correlate those windows with the applicable first, second and third reference planes 534, 536, and 538 in the front-view CBCT image 210. For ease of reference in the figures, the borders are shown with corresponding dashed and dotted lines.

Similar to the discussion regarding the landmark indicators in the planning procedure, the first landmark indicator 514 represents an interactive indicator for locating the first landmark point on the front-view CBCT image 210 of the patient using a probe (e.g., a drill tip or a probe tip) during the matching procedure in order to match or register its location on the patient. Specifically, when the first landmark indictor 514 is active (either by the user selecting it or automatically as part of the procedure), the user moves the probe in the area of interest on the patient, the location of the probe is shown on the front-view CBCT image 210. In aspects, the first landmark indicator 514 when highlighted (or otherwise identified as "active") indicates that the first landmark point is active for being located on the patient and front-view CBCT image 210 during the landmark matching procedure.

The front-facing enlarged CBCT image 504A includes a cross marker 220A that corresponds to a first landmark point 220 in the front-view CBCT image 210 on the patient's anatomy 550. The patient's anatomy 550 in the CBCT image 210 may include coloring or shading to indicate anatomical features, such as bones, nerves, blood vessels, and other features of the anatomy.

The side-facing enlarged CBCT image 506A includes a cross marker 220B that corresponds to the first landmark point 220 in the front-view CBCT image 210.

The downward-facing enlarged CBCT image 508A includes a cross marker 220C that corresponds to the first landmark point 220 in the front-view CBCT image 210.

The front-view CBCT image 210 includes a jawbone 12, the first landmark point 520 (e.g., at a point marked as '1' in FIG. 5), a circular indicator 532, the front-facing reference plane 534, the side-facing reference plane 536 and the downward-facing reference plane 538. In aspects, the circular indicator 532 represents a highlight marker in which a center of the circle corresponds to the first landmark point 220 for clarity in the user interface.

The first landmark point 220 is interactively located by pointing and touching with a probe (such as the drill tip) on the physical anatomy at a location on the patient. For purposes of proper registration, the first landmark point that is selected on the patient must correspond with the first landmark point 220 (as shown in FIG. 2) that was previously selected during the landmark planning procedure. Once matched, the first landmark point 220 is deemed registered and defines one of the three or more registered landmark points in the landmark matching procedure.

FIG. 6 illustrates the graphical user interface 500 showing an example graphical image of the system during the matching procedure for locating the second landmark for registration according to an embodiment of the invention.

In aspects, the graphical user interface 500 includes a second landmark indicator 516, the first window 504 illustrating an enlarged view of a front-facing CBCT image 604A, the second window 506 illustrating an enlarged view of a side-facing CBCT image 606A, the third window 508 illustrating an enlarged view of a downward-facing CBCT image 608A, and the front-view CBCT image 310.

The second landmark indicator 516 represents an interactive indicator for selecting the second landmark point on the patient that matches the second landmark point located during the planned procedure. The second landmark indicator 516 is activated similar to the indicators discussed above. When activated, the second landmark indicator 516 indicates that the second landmark point is active for locating the second landmark point 320 on the patient.

The front-facing CBCT image 604A includes a cross marker 320A that corresponds to the second landmark point 320 in the front-view CBCT image 310. As discussed above, the graphical user interface 500 includes indicia to correlate images shown in the first, second, and third windows 504, 506, 508 with the corresponding first, second and third reference planes 634, 636, 638 in the front-view CBCT image 310.

The side-facing CBCT image 606A includes a cross marker 320B that corresponds to the second landmark point 320 in the front-view CBCT image 310.

The downward-facing CBCT image 608A includes a cross marker 320C that corresponds to the second landmark point 320 in the front-view CBCT image 310.

As mentioned above, the front-view CBCT image 310 depicts a front view of the patient's anatomy (although the view can be varied by the user as needed). The front-view CBCT image 310 includes the second landmark point 320 (e.g., at a point marked as '2' in FIG. 6), the circular indicator 632, the front-facing first reference plane 634, the side-facing second reference plane 636 and the downward-facing third reference plane 638. In aspects, the circular indicator 632 represents a highlight marker in which a center of the circle corresponds to the second landmark point 320.

The second landmark point 320 is interactively determined by the clinician using a probe (e.g., a drill tip) to point to and physically touch a location on the patient's anatomy 550 which corresponds to the second landmark point 320 in the front-view CBCT image 510. The second landmark point that is selected must correspond with the second landmark point 320 that was selected during the planning procedure. Once matched, the second landmark point 320 represents a second registered landmark point of the three or more registered landmark points in the landmark matching procedure.

A distance indicator 614 is provided and indicates, in real time, a distance between a location of the drill tip and an expected location of the second landmark point for determination during the landmark matching procedure. As discussed above, the expected location of the second landmark point 320 is determined based on the location of the first landmark point 220 as registered, and the known distance between the first landmark point 220 and the second landmark point 320 that were selected during the landmark planning procedure. In the depicted figure, the distance of the drill tip is shown, for example, as being 2.2 millimeters away from the expected location of the second landmark point 320 that was identified during the landmark planning procedure. The clinician moves the drill tip a distance of 2.2 mm in the appropriate direction on the patient's anatomy (e.g., in the patent's mouth) so as to eliminate the deviation between the expect second landmark location and the actual drill tip location, thereby matching the second landmark point. In the illustrated embodiment, the distance indicator is shown as a colored or shaded bar and actively changes in length as the user moves the drill tip relative to the second landmark point 320.

The circular indicator 632 is centered on the second landmark point 320 indicates that the second landmark point is selection is active and identifies on the image where the point is generally located. It is contemplated that the size of the circular indicator 632 can be adjusted to provide a visual indication of the amount of deviation of the probe tip location from the center at the second landmark point 320. In aspects, the size (e.g., diameter) of the circular indicator 632 changes to indicate the relative distance of the probe tip (i.e., the drill tip) from the expected second landmark point 320. As illustrated in the figure, the size of the indicator represents that the actual probe location is currently somewhere distant from the expected second landmark point 320.

In aspects, the distance indicator 614 is a deviation gauge that reports a "live" error distance, which is a difference between (i) a distance between the registered first landmark point (not shown) and the second landmark point 320 as identified during the planning procedure and (ii) a distance between the first landmark point 220 as registered and the current location of probe tip. As the user moves the probe tip the difference changes and moves toward zero as the probe tip gets closer to the previously identified second landmark point and becomes zero when the probe tip is at the identified second landmark point 320 . . . . Similarly, the distance depicted increases as the probe tip moves away from the identified second landmark point. The circular indicator 632 may also be depicted in a two-dimensional CT slice it intersects. In some other aspects, the deviation information may be conveyed in a tabular form (the table), iconic form (the deviation gauge), a two-dimensional anatomical overlay, a three-dimensional anatomical overlay, and the like.

FIG. 7 illustrates the graphical user interface 500 from FIG. 6 after the user has repositioned the probe such that the deviation between the probe location and the second landmark point 320 is reduced to zero. The distance indicator 614 indicates a zero distance between the location of the probe and an expected location of the second landmark point indicating a match. The clinician selects or otherwise causes the system to register the second landmark point.

FIG. 8 illustrates the graphical user interface 500 showing an example graphical image of the system during the matching procedure for locating the third landmark point for registration.

The graphical user interface 500 includes a third landmark indicator 420, a front-facing CBCT image 804A in the first window 504, a side-facing CBCT image 806A in the second window 506, a downward-facing CBCT image 808A in the third window 508, and the front-view CBCT image 410.

Similar to the second landmark indicator 516, the third landmark indicator 518 represents an interactive indicator for locating the third landmark point on the patient that matches the third landmark point 420 selected during the planned procedure. The third landmark indicator 518 is activated similar to the indicators discussed above. When activated, the third landmark indicator 518 indicates that the third landmark point is active for determination.

The front-facing CBCT image 804A includes a cross marker 420A that corresponds to a third landmark point 420 in the front-view CBCT image 410. As discussed above, the graphical user interface 500 includes indicia to correlate images shown in the first, second, and third windows with the corresponding first, second and third reference planes 834, 836, 838 in the front-view CBCT image 410.

The side-facing CBCT image 806A includes a cross marker 420B that corresponds to the third landmark point 420 in the front-view CBCT image 510.

The downward-facing CBCT image 808A includes a cross marker 420C that corresponds to the third landmark point 420 in the front-view CBCT image 410.

The front-facing CBCT image 410 includes the third landmark point 420 (e.g., at a point marked as '3' in FIG. 8), a circular indicator 832, the front-facing first reference plane 834, the side-facing second reference plane 836 and the downward-facing third reference plane 838. In aspects, the circular indicator 832 represents a highlight marker in which a center of the circle corresponds to the third landmark point 420.

The third landmark point 420 is interactively determined by the clinician using a probe (e.g., a drill tip) to point to and physically touch a location on the patient corresponding to the third landmark point 420 in the front-view CBCT image 410. The third landmark point 420 that is selected must correspond with the third landmark point 420 (as shown in FIG. 4) that was selected during the planning procedure. Once matched, the third landmark point 420 represents a third registered landmark point of the three or more registered landmark points in the landmark matching procedure.

Similar to the discussion with respect to FIG. 6, a distance indicator 814 is provided which indicates, in real time, a distance between the location of the probe and an expected location of the third landmark point for determination during the landmark matching procedure. As discussed above, the expected location of the third landmark point is determined based on the locations of the first landmark point 220 as registered, the second landmark point 320 as registered, as well as the distance between the first and second landmark points 220, 320 selected during the landmark planning procedure and the third landmark point 420 selected during the landmark planning procedure. In the depicted figure, the distance of the drill tip is shown as being 2.2 mm away from the expected location of the third landmark point 420. The clinician moves the drill for 2.2 mm in the appropriate direction on the patent's anatomy (e.g., in the patent's mouth) so as to eliminate the deviation between the expect second landmark location and the actual drill tip location thereby matching the third landmark point.

FIG. 9 illustrates the graphical user interface 500 from FIG. 8 after the user has repositioned the probe such that the deviation between the probe location and the third landmark point 420 is reduced to zero and the third landmark point has been registered.

The first window 504, the second window 506, and the third window 508 appear blank to indicate that the third landmark point has been registered.

Figure 10:
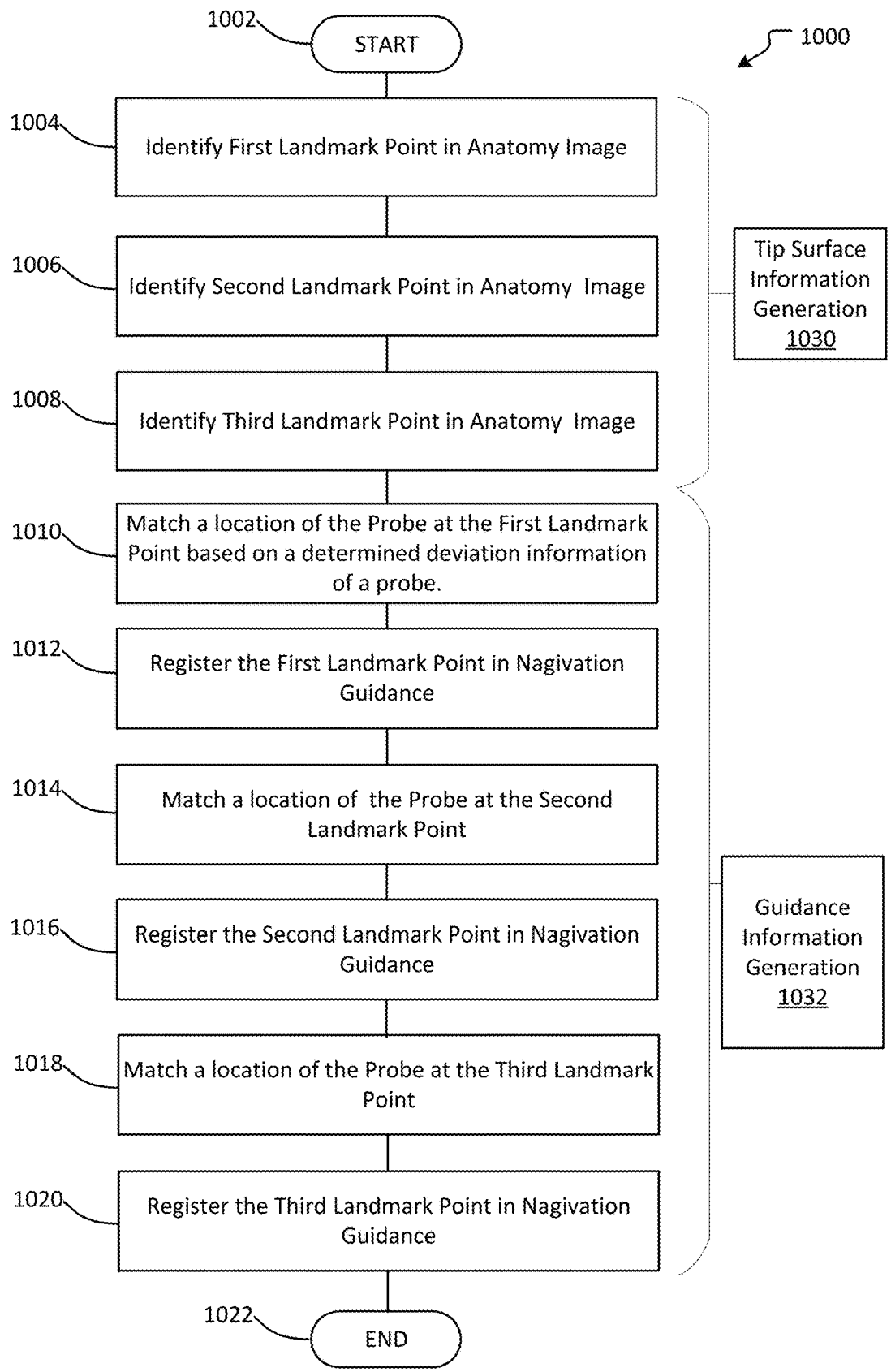
FIG. 10 illustrates an exemplary method for planning and registering landmark points according to the invention.

FIG. 10 illustrates an example method for planning and matching landmark points according to the present invention. The present invention contemplates planning and matching three or more landmark points for registration prior to a surgery procedure that uses a navigational surgery support system. A general order of the operations for the example method 1000 is shown in FIG. 10. Generally, the method 1000 begins with start operation 1002 and ends with end operation 1022. The method 1000 may include more or fewer steps or may arrange the order of the steps differently than those shown in FIG. 10.

The method 1000 can be executed as a set of computer-executable instructions executed by a computer processor in a cloud based or land based system and encoded or stored on a computer readable medium. Further, the method 1000 can be performed by gates or circuits associated with a processor, an ASIC, an FPGA, a SOC or other hardware device. Hereinafter, the method 1000 shall be explained with reference to the systems, components, devices, modules, software, data structures, data characteristic representations, signaling diagrams, methods, etc., described in conjunction with FIGS. 1, 2, 3, 4, 5, 6, 7, 8, 9, and 11.

Following start operation 1002, the method 1000 begins with an identify first landmark point operation 1004, which identifies a first landmark point in an anatomy image. In aspects, the anatomy image comprises CT and/or CBCT images of a patient. In examples, the identify first landmark point operation 1004 comprises operations by a clinician to interactively select a location of a first landmark point in the anatomy image.

At an identify second landmark point operation 1006, a second landmark point is interactively identified in the anatomy image. In aspects, the clinician uses a graphical user interface to select the second landmark point in the anatomy image.

At an identify third landmark point operation 1008, a third landmark point is interactively identified in the anatomy image. In aspects, the clinician uses a graphical user interface to select the third landmark point in the anatomy image. In examples, the system stores information on the identified first, second, and third landmark points in a database (e.g., the anatomy information 108 as shown in FIG. 1).

At a matching first landmark point operation 1010, the first landmark point is determined by the clinician interactively placing a probe at the planned first landmark point on the patient. In aspects, the clinician uses a graphical user interface to monitor the expected first landmark point in the anatomy image and a location of the drill.

At a register first landmark point operation 1012, the determined first landmark point is registered as a part of the guidance information (e.g., the navigation guidance information 110 as shown in FIG. 1).

At a matching second landmark point operation 1014, the second landmark point is determined by the clinician interactively placing a drill at the planned second landmark point on the patient. In aspects, the clinician uses a graphical user interface to monitor the expected second landmark point in the anatomy image and a location of the drill.

At a register second landmark point operation 1016, the determined second landmark point is registered as a part of the guidance information (e.g., the navigation guidance information 110 as shown in FIG. 1).

At a matching third landmark point operation 1018, the third landmark point is determined by the clinician interactively placing a drill at the planned third landmark point on the patient. In aspects, the clinician uses a graphical user interface to monitor the expected third landmark point in the anatomy image and a location of the drill.

At a register third landmark point operation 1020, the determined third landmark point is registered as a part of the guidance information (e.g., the navigation guidance information 110 as shown in FIG. 1). The method 1000 ends with the end operation 1022.

In aspects, a set of the identify first landmark point operation 1004, the identify second landmark point operation 1006, and the identify third landmark point operation 1008 is a least a part of tip surface information generation 1030. In examples, the tip surface information is generated and stored as a part of the anatomy information (e.g., the anatomy information 108 as shown in FIG. 1).

In aspects, a set of operations from the matching first landmark point operation 1010 through the register third landmark point operation 1020 is at least a part of a guidance information generation 1032. The guidance information may correspond to the navigation guidance information (e.g., the navigation guidance information 110 as shown in FIG. 1) used for performing navigational guidance during a surgery.

Additionally, or alternatively the system automatically identifies one or more landmark points of the first, second and third landmark points by automatically executing the identify first landmark point operation 1004, the identify second landmark point operation 1006, and the identify third landmark point operation 1008 as a part of an automated operation of the tip surface information generation 1030. In examples, the system identifies the second and third landmark points along a ridge of a predetermined distance from a primary midline point. The primary midline point corresponds to the first landmark point for planning.

As should be appreciated, operations 1002-1022 are described for purposes of illustrating the present methods and systems and are not intended to limit the disclosure to a particular sequence of steps, e.g., steps may be performed in different order, additional steps may be performed, and disclosed steps may be excluded without departing from the present disclosure.

Figure 11:
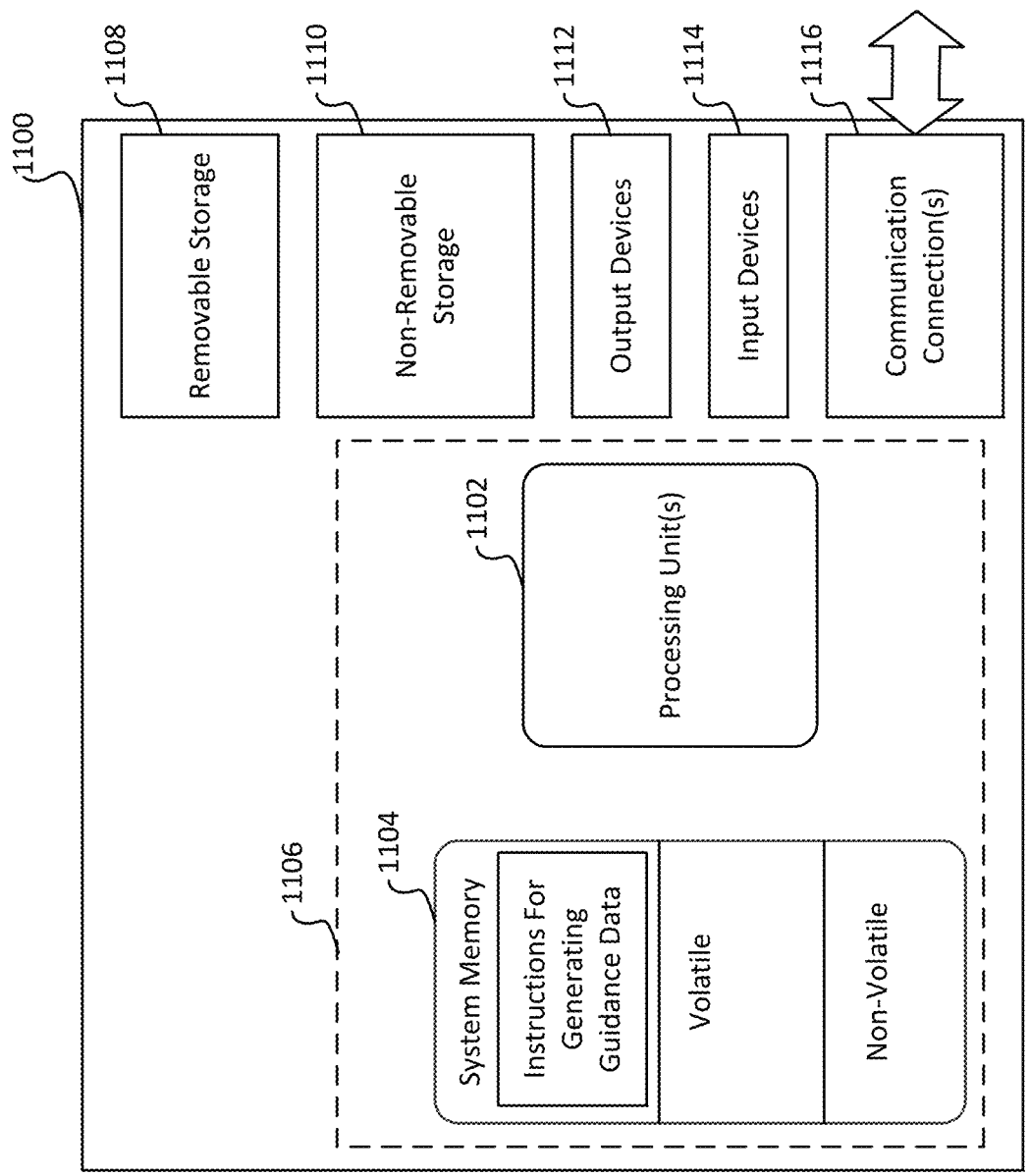
FIG. 11 illustrates a simplified block diagram of a device with which aspects of the present disclosure may be practiced in accordance with aspects of the present disclosure.

FIG. 11 illustrates a simplified block diagram of a device with which aspects of the present disclosure may be practiced in accordance with aspects of the present disclosure. The device, which represents at least a part of a surgical navigation system, may be a mobile computing device, for example. One or more of the present embodiments may be implemented in an operating environment 1100. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smartphones, network PCs, minicomputers, mainframe computers, distributed computing environments that include any of the above systems or devices, and the like.

In its most basic configuration, the operating environment 1100 typically includes at least one processing unit 1102 and memory 1104. Depending on the exact configuration and type of computing device, memory 1104 may be volatile (such as RAM), non-volatile (such as ROM, flash memory, etc.), or some combination of the two. This most basic configuration is illustrated in FIG. 11 by dashed line 1106. Further, the operating environment 1100 may also include storage devices (removable, 1108, and/or non-removable, 1110) including, but not limited to, magnetic or optical disks or tape. Similarly, the operating environment 1100 may also have input device(s) 1114 such as remote controller, keyboard, mouse, pen, voice input, on-board sensors, etc. and/or output device(s) 1112 such as a display, speakers, printer, motors, etc. Also included in the environment may be one or more communication connections 1116, such as LAN, WAN, a near-field communications network, a cellular broadband network, point to point, etc.

Operating environment 1100 typically includes at least some form of computer readable media. Computer readable media can be any available media that can be accessed by the at least one processing unit 1102 or other devices comprising the operating environment. By way of example, and not limitation, computer readable media may comprise computer recording media and communication media. Computer recording media includes volatile and nonvolatile, removable and non-removable media implemented in any method or technology for storage of information such as computer readable instructions, data structures, program modules or other data. Computer recording media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible, non-transitory recording medium which can be used to store the desired information. Computer recording media does not include communication media. Computer recording media does not include a carrier wave or other propagated or modulated data signal. As used herein memory and other storage devices may be configured for storing data (such as image data, models, location data) and/or computer-executable instructions defining and/or associated with a processor for carrying out some or all of the processing or system steps described herein, and the processor may retrieve and execute those instructions as contemplated herein.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The operating environment 1100 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet. Any of the one or more above aspects in combination with any other of the one or more aspect. Any of the one or more aspects as described herein.

The computer processes herein may be described in terms of various processing steps. Such processing steps may be realized by any number of hardware and/or software components that perform the specified functions. Aspects of the present disclosure may be implemented using hardware, software, or a combination thereof and may be implemented in one or more computer systems or other processing systems. In one aspect, the disclosure is directed toward one or more computer systems capable of carrying out the functionality described herein.

The computer programs (also referred to as computer control logic, programming logic, or programming) are stored in the memory. Computer programs may also be received via a communications interface. Such computer programs, when executed, enable the computer system to perform various features in accordance with aspects of the present disclosure, as discussed herein. In particular, the computer programs, when executed, enable the processor to perform such features. Accordingly, such computer programs represent controllers of the computer.

It is understood by those skilled in the art that the location information that is utilized by the processor may be from signals received by the processor from internal or external sources such as data files, external inputs (mouse clicks, keyed entries, etc.), or analyzed from other data provided to the processor.

The description and illustration of one or more aspects provided in this application are not intended to limit or restrict the scope of the disclosure as claimed in any way. The aspects, examples, and details provided in this application are considered sufficient to convey possession and enable others to make and use claimed aspects of the disclosure. The claimed disclosure should not be construed as being limited to any aspect, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

The invention claimed is:

1. A method for registering landmark points for image guided surgery, comprising the steps of:

identifying a location of a first landmark point of at least three landmark points in an anatomy image;
identifying, based on an anatomical feature in the anatomy image, a location of a second landmark point of the at least three landmark points in the anatomy image;
identifying, based on an anatomical feature in the anatomy image, a location of a third landmark point of the at least three landmark points in the anatomy image;
storing the identified first landmark point location, the identified second landmark point location and the identified third landmark point location;
receiving probe location information corresponding to real-time locations of a probe tip on a patient's anatomy;
matching a first probe location of the probe location information with the identified first landmark point location and storing the first probe location as a first registered landmark point;
determining first deviation information based on the probe location information;
displaying the first deviation information;
matching a second probe location with the identified second landmark point location when the first deviation information is below a threshold and storing the second probe location as a second registered landmark point;
determining second deviation information based on the probe location information;
displaying the second deviation information;
matching a third probe location with the identified third landmark point location when the second deviation information is below a threshold and storing the third probe location as a third registered landmark point; and
generating, based on the first, second and third registered landmark points, navigational guidance information for performing a surgery operation on the anatomy.

2. The method according to claim 1, wherein the anatomy image comprises a combination of intraoral scan data and computed tomography ("CT") image data.

3. The method according to claim 1, wherein the step of generating navigational guidance information further comprises:
using the first, second and third registered landmark points to correlate the positional data of a surgical tool location relative to a patient's anatomy with a CT scan of the patient's anatomy;
generating and presenting on a display during a surgical procedure a representation of a surgical tool on the CT image based on real time data received on the location of the surgical tool during a surgical operation.

4. The method according to claim 1, wherein the first deviation information is based on at least one of (i) the first registered landmark point and (ii) the identified first landmark point location; and the identified second landmark point location.

5. The method according to claim 1, wherein the first deviation information is based on a difference between a first distance and a second distance, wherein the first distance is the distance between the identified first landmark point location and the identified second landmark point location, and the second distance is the distance between (i) one of either the identified first landmark point location or the first registered landmark point, and (ii) the probe location information corresponding to a current location of the probe tip.

6. The method according to claim 5, wherein the second deviation information is based on (a) at least one of (i) the first registered landmark point, (ii) the identified first landmark point location, (iii) the second registered landmark point, and (iv) the identified second landmark point location; and (b) the identified third landmark point location.

7. The method according to claim 5, wherein the second deviation information is based on a difference between a third distance and a fourth distance, wherein the third distance is the distance between (a) one of either the identified first landmark point location or the first registered landmark point, and (b) the identified third landmark point location, and the fourth distance is the distance between (c) one of either the identified first landmark point location or the first registered landmark point, and (d) the probe location information corresponding to a current location of the probe tip.

8. The method according to claim 1, wherein the step of receiving probe location information comprises receiving a stream of location data corresponding to the changing location of the probe tip as it moves; wherein the first deviation information changes based on changes in the probe location information; and wherein the second deviation information changes based on changes in the probe location information.

9. The method according to claim 1, wherein the anatomical feature is detected by defining a mesh representation corresponding to at least a portion of a surface in the anatomy image; analyzing geometries of the mesh representation for identifying local morphological characteristics representation of anatomical features; and selecting the anatomical feature.

10. The method according to claim 1, wherein the first location of the first landmark point corresponds to a location of a fiducial attached to the anatomy of the patient.

11. The method according to claim 1, further comprising:
displaying the anatomy image; and
interactively receiving an input in the anatomy image, the input specifying the second landmark point location of the at least three landmark points in the anatomy image.

12. The method according to claim 1, wherein the second location of the second landmark point is selected to be on a crest of a bone ridge of a jawbone as determined by a trained machine learning model, and the trained machine learning model predicts the crest of the bone ridge in an arch of points as along a midline of the jawbone in the anatomy image based on the anatomy image as input.

13. A system for registering landmark points as a pre-surgery procedure, the system comprises one or more processors configured to execute operations comprising:
identifying a location of a first landmark point in an anatomy image;
identifying, based on an anatomical feature detected in the anatomy image, a location of a second landmark point in the anatomy image;
identifying, based on an anatomical feature detected in the anatomy image, a location of a third landmark point in the anatomy image;
storing the identified first landmark point location, the identified second landmark point location and the identified third landmark point location;
receiving probe location information corresponding to real-time locations of a probe tip on a patient's anatomy;
matching a first probe location of the probe location information with the identified first landmark point location and storing the first probe location as a first registered landmark point;
determining first deviation information based on the probe location information;
displaying the first deviation information;

matching a second probe location with the identified second landmark point location when the first deviation information is below a threshold and storing the second probe location as a second registered landmark point;
determining second deviation information based on the probe location information;
displaying the second deviation information;
matching a third probe location with the identified third landmark point location when the second deviation information is below a threshold and storing the third probe location as a third registered landmark point; and
generating, based on the first, second and third registered landmark points, navigational guidance information for performing a surgery operation on the anatomy.

14. The system according to claim 13, wherein the step of generating navigational guidance information comprises:
using the first, second and third registered landmark points to correlate the positional data of a surgical tool location relative to a patient's anatomy with a CT scan of the patient's anatomy;
generating and presenting on a display during a surgical procedure a representation of a surgical tool on the CT image based on real time data received on the location of the surgical tool during a surgical operation.

15. The system according to claim 13, wherein the first deviation information is based on at least one of (i) the first registered landmark point and (ii) the identified first landmark point location; and the identified second landmark point location.

16. The system according to claim 15, wherein the first deviation information is based on a difference between a first distance and a second distance, wherein the first distance is the distance between the identified first landmark point location and the identified second landmark point location, and the second distance is the distance between (i) one of either the identified first landmark point location or the first registered landmark point, and (ii) the probe location information corresponding to a current location of the probe tip.

17. The system according to claim 16, wherein the second deviation information is based on (a) at least one of (i) the first registered landmark point, (ii) the identified first landmark point location, (iii) the second registered landmark point, and (iv) the identified second landmark point location; and (b) the identified third landmark point location.

18. The system according to claim 17, wherein the second deviation information is based on a difference between a third distance and a fourth distance, wherein the third distance is the distance between (a) one of either the identified first landmark point location or the first registered landmark point, and (b) the identified third landmark point location, and the fourth distance is the distance between (c) one of either the identified first landmark point location or the first registered landmark point, and (d) the probe location information corresponding to a current location of the probe tip.

19. The system according to claim 13, wherein the step of receiving probe location information comprises receiving a stream of location data corresponding to the changing location of the probe tip as it moves; wherein the first deviation information changes based on changes in the probe location information; and wherein the second deviation information changes based on changes in the probe location information.

20. The system according to claim 13, wherein the anatomical feature is detected by defining a mesh representation corresponding to at least a portion of a surface in the anatomy image; analyzing geometries of the mesh representation for identifying local morphological characteristics representation of anatomical features; and selecting the anatomical feature.

21. The system according to claim 13, wherein the identified first landmark point location corresponds to a location of a fiducial attached to the anatomy of the patient.

22. The system according to claim 13, the processor further configured to execute operations comprising:
displaying the anatomy image; and
interactively receiving an input in the anatomy image, the input specifying the second landmark point location in the anatomy image.

23. The system according to claim 13, wherein the second landmark point location is selected to be on a crest of a bone ridge of a jawbone as determined by a trained machine learning model, and the trained machine learning model predicts the crest of the bone ridge in an arch of points as along a midline of the jawbone in the anatomy image based on the anatomy image as input.

24. A non-transitory computer-readable recording medium storing a computer-executable program instructions that when executed by at least one processor cause a computer system to execute operations comprising:
identifying a location of a first landmark point in an anatomy image;
identifying, based on an anatomical feature detected in the anatomy image, a location of a second landmark point in the anatomy image;
identifying, based on an anatomical feature detected in the anatomy image, a location of a third landmark point in the anatomy image;
storing the identified first landmark point location, the identified second landmark point location and the identified third landmark point location;
receiving probe location information corresponding to real-time locations of a probe tip on a patient's anatomy;
assigning a first probe location of the probe location information to the identified first landmark point location and storing the first probe location as a first registered landmark point;
determining first deviation information based on the probe location information;
displaying the first deviation information;
matching a second probe location with the identified second landmark point location when the first deviation information is below a threshold and storing the second probe location as a second registered landmark point;
determining second deviation information based on the probe location information;
displaying the second deviation information;
matching a third probe location with the identified third landmark point location when the second deviation information is below a threshold and storing the third probe location as a third registered landmark point; and
generating, based on the first, second and third registered landmark points, navigational guidance information for performing a surgery operation on the anatomy.

25. The non-transitory computer-readable recording medium according to claim 24, wherein the step of generating navigational guidance information comprises;
using the first, second and third registered landmark points to correlate the positional data of a surgical tool location relative to a patient's anatomy with a CT scan of the patient's anatomy;
generating and presenting on a display during a surgical procedure a representation of a surgical tool on the CT image based on real time data received on the location of the surgical tool during a surgical operation.

26. The non-transitory computer-readable recording medium according to claim 24, wherein the first deviation information is based on a difference between a first distance and a second distance, wherein the first distance is the distance between the identified first landmark point location and the identified second landmark point location, and the second distance is the distance between (i) one of either the identified first landmark point location or the first registered landmark point, and (ii) the probe location information corresponding to a current location of the probe tip.

27. The non-transitory computer-readable recording medium according to claim 24, wherein the second deviation information is based on a difference between a third distance and a fourth distance, wherein the third distance is the distance between (a) one of either the identified first landmark point location or the first registered landmark point, and (b) the identified third landmark point location, and the fourth distance is the distance between (c) one of either the identified first landmark point location or the first registered landmark point, and (d) the probe location information corresponding to a current location of the probe tip.

\* \* \* \* \*

UNITED STATES PATENT AND TRADEMARK OFFICE
CERTIFICATE OF CORRECTION

PATENT NO. : 12,396,804 B2
APPLICATION NO. : 19/027752
DATED : August 26, 2025
INVENTOR(S) : Jason Gibbs et al.

Page 1 of 1

It is certified that error appears in the above-identified patent and that said Letters Patent is hereby corrected as shown below:

On the Title Page

Item (75) "Inventors" should read:
(75) Inventors: Jason Gibbs, State College, PA (US);
Scott A. Merritt, Green Lane, PA (US);
Robert W. Emery, III, Mclean, VA (US);
Pascal Kunz, Oberwil-Lieli (CH);
Edward J. Marandola, Gwynedd, PA (US);
Christopher W. Scharff, Collegeville, PA (US)

Signed and Sealed this
Ninth Day of December, 2025

John A. Squires
*Director of the United States Patent and Trademark Office*